United States Patent [19]

Kielpikowski et al.

[11] Patent Number: 4,842,596
[45] Date of Patent: Jun. 27, 1989

[54] METHOD OF MAKING A BREATHABLE ELASTIC FABRIC COMPOSITE AND PERSONAL ARTICLE INCORPORATING SAME

[75] Inventors: David P. Kielpikowski, Appleton; Duane G. Uitenbroek, Little Chute, both of Wis.

[73] Assignee: Kimberly-Clark Corporation, Neenah, Wis.

[21] Appl. No.: 947,949

[22] Filed: Dec. 31, 1986

[51] Int. Cl.$^4$ .............................................. A61F 13/16
[52] U.S. Cl. .................................. 604/385.2; 604/393
[58] Field of Search ...................... 604/393, 394, 385.1, 604/383, 389

[56] References Cited

U.S. PATENT DOCUMENTS

| | | | |
|---|---|---|---|
| 4,022,210 | 5/1977 | Glassman | 128/284 |
| 4,166,464 | 9/1979 | Korpman | 604/378 |
| 4,515,595 | 5/1985 | Kievit et al. | 604/385.2 |
| 4,573,991 | 3/1986 | Pieniak et al. | 604/366 |
| 4,615,695 | 10/1986 | Cooper | 604/385 |
| 4,710,187 | 12/1987 | Boland et al. | 604/385.1 |
| 4,770,656 | 9/1988 | Proxmire et al. | 604/393 |

*Primary Examiner*—C. Fred Rosenbaum
*Assistant Examiner*—Mark O. Polutta
*Attorney, Agent, or Firm*—John L. Chiatalas

[57] ABSTRACT

A method for making a breathable elastomeric laminar fabric, the material produced thereby and a disposable absorbent garment incorporating the material as either an outer cover or gathers at the leg and waist openings. The method comprises the steps of sandwiching a liquid impermeable elastomeric film or nonwoven carrier sheet between a pair of nonwoven facing sheets while the carrier sheet is in at least a partially stretched condition and bonding the facing sheets together through the carrier sheet at spaced apart sites, simultaneously forming breathable apertures while laminating the carrier and facing sheets together at the spaced apart sites. Creped facing sheets may also be used and bonded together while the film is in a partially stretched or unstretched condition.

9 Claims, 10 Drawing Sheets

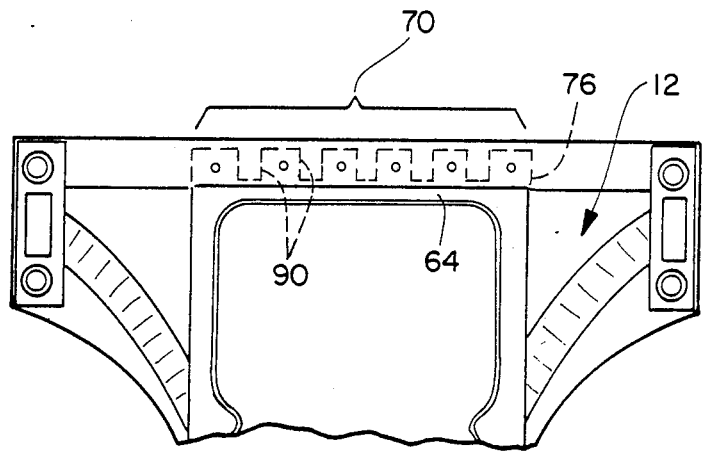
FIG. 12
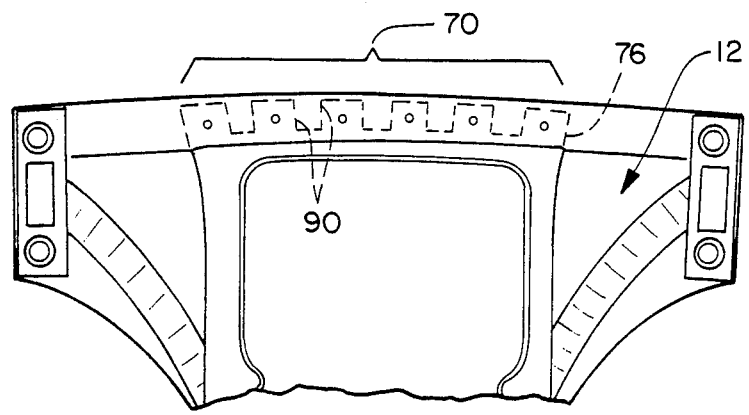
FIG. 13

METHOD OF MAKING A BREATHABLE ELASTIC FABRIC COMPOSITE AND PERSONAL ARTICLE INCORPORATING SAME

TECHNICAL FIELD

The present invention relates, generally, to the field of disposable garments utilized for the absorption and containment of urine and other bodily exudates. More particularly, the present invention relates to leg and waist gathers for form-fitting self-adjusting disposable absorbent garments and to garments, such as disposable diapers, incorporating such gathers.

BACKGROUND OF THE INVENTION

This invention is an improvement upon the disposable garment of U.S. patent application Ser. Nos. 902,828 and 902,830, both filed Sept. 3, 1986 and assigned to the instant assignee, the entire disclosures of which are expressly incorporated herein by reference and relied upon. The following U.S. patent application Ser. Nos., concurrently filed herewith, are also expressly incorporated herein by reference and relied upon: 947,942, now U.S. Pat. No. 4,808,176; 947,941, now abandoned; 947,947, now U.S. Pat. No. 4,770,656; 947,948, now abandoned, all filed Dec. 31, 1987.

Disposable garments are generally well known in the art and have become an important and an essentially indispensable sanitary protection item, most particularly in the field of infant and child care where disposable diapers provide for the absorption and containment of urine and other bodily exudates. Present commercially available disposable diapers are generally unitary, preshaped and prefolded, and comprised of a porous facing layer, a fluid impervious backing sheet with an absorbent material disposed therebetween. These presently available disposable diapers have met a particular need and have become ever increasingly popular. However, even though the present available disposable diapers have achieved a certain degree of efficiency and effectiveness, several draw-backs remain that have been identified by mothers of infants wearing the diapers. These mothers have strongly voiced their desire to be able to obtain disposable diapers that are aesthetically neat and attractive when on their infant or child. The aesthetically neat criteria have been identified as including a trim, slim fit, and a neat fitting waist and legs that do not allow leakage of urine or feces. It has also been found that mothers do not want their children looking rumpled, bulky or messy. In addition, these mothers have expressed the desire to either have a disposable diaper that fits more sizes of babies or to have disposable diapers provided in more sizes. Another draw-back identified by these mothers has been the problem associated with skin irritation caused by urine, feces or moisture trapped next to the skin. They have again been very vocal in their desire to obtain disposable diapers that avoid or solve this problem.

A variety of prior diaper constructions have used leg or waist gathers. For example, U.S. Pat. No. 4,324,245 to Mesek, et al., discloses a gathered or bloused design wherein waterproof extruded elastic film is applied to the waist and leg areas of a film barrier backsheet having an absorbent adhered thereto so that the elastic deforms the absorbent structure; again, such an arrangement represents the current state of disposable diapers on the market. Others include U.S. Pat. No. 3,196,872 to Hrubecky showing a rectangular diaper provided with triangular-shaped infolds in the crotch area, U.S. Pat. No. 3,860,003 to Buell wherein the diaper edges are provided with elasticized, flexible flaps along the edge of the absorbent pad in the crotch region and U.S. Pat. No. 4,050,462 to Woon, et al. wherein the diaper is elasticized only along the edges in the narrowed crotch area to create gross transverse rugosities in the crotch area.

Prior art constructions, such as U.S. Pat. No. 3,658,064 to Pociluyko and U.S. Pat. No. 3,370,590 to Hokanson, et al. have attempted to provide waste containment with a reusable liquid impermeable diaper cover having waterproof pouches or pockets for freely receiving an absorbent, such as a traditional cloth diaper or disposable absorbent; however, the retaining pouches on these supporting garments occlude the skin, covering the target areas at which urine is excreted. U.S. Pat. No. 4,425,128 to Motomura, discloses a diaper cover with sections of waterproof and stretching material in the cover adjacent the fasteners. U.S. Pat. No. 2,141,105 is similar, nevertheless, such constructions rely upon reuseable treated woven fabric and many have seams to fully integrate other nonstretchable absorbent components between stretchable diaper ears, effectively eliminating any stretch properties in the front or rear panels or along the waist and leg openings of the diaper cover. Moreover, there is no recognition of a functional absorbent structure integrated into a stretchable outer cover providing cooperative interactions therebetween to enhance the fit, appearance and containment of the diapering system.

Other approaches have utilized elastic fluid impermeable backing films laminated to an absorbent layer in an attempt to provide enhanced conformability to the body surface, but these films are occlusive to the skin, there is no cooperation of elements elucidated and the integration of the absorbent component restricts the elasticity of the outer cover by the manner in which it is bonded thereto. In this type of construction, the elastic backing film must provide both the barrier function and the fit and conformability functions of the diaper. Such an absorbent dressing is taught by U.S. Pat. No. 4,166,464 to Korpman.

U.S. Pat. No. 4,397,646 to Daniels, et al. discloses a reuseable diaper capable of repeated sterilizations in a diaper laundry, comprising elasticized end and side margins and a durable absorbent such as cotton sewn into the crotch area of the waterproof diaper cover, which is a Teflon ® coated polyester or equivalent woven material.

U.S. Pat. Nos. 4,597,761, 4,496,360 and 4,597,670 all disclose multi-component diapering systems comprising a disposable absorbent capable of attachment to a reusable overgarment. U.S. Pat. Nos. 4,355,425 to Jones, et al., which uses a melt-blown elastic border strip, and 3,644,157 to Draper both disclose disposable stretchable panties or shorts unsuitable for use as diapering garments.

U.S. Pat. No. 4,573,991 to Pieniak discloses a reticulated elastic member secured between the facing and film backing sheets of a diaper. U.S. Pat. No. 4,606,964 to Wideman discloses a pleated web bonded to an elastomeric film, however, breathability is not simultaneously imparted to the composite by the bonding process. Various non-elastomeric films require stretching to impart porosity therein. U.S. Pat. No. 4,525,407 to Ness discloses a laminate rendered elastic by stretching.

In summary, presently available disposable diapers utilize nonstretchable backsheets functioning both as the diaper cover and liquid barrier with absorbent adhered thereto and fastenable around the wearer via tapes; even where prior art designs have attempted to use impermeable elastic film barriers, there has been inadequate recognition of the associated problems. Prior art diaper covers, reusable for holding an absorbent, do not address the many substantial interactive concerns presented by a separate absorbent insert, stretchable outer cover, leg and waist gathers and a fastening system. There is a need for making breathable elastomeric nonwoven laminar fabrics from waterproof nonadhesive elastic carrier sheets in a one-step process and for garments incorporating such materials. There is a further need for form-fitting, self-adjusting disposable absorbent garments incorporating breathable gathers in achieving a synchronous functionality of the combined diapering system.

SUMMARY OF THE INVENTION AND ADVANTAGES

According to the invention there is provided a method for making a breathable elastomeric nonwoven laminar fabric for use in a personal absorbent article. The method comprises the steps of providing a liquid impermeable and nonself-adhering elastomeric film or nonwoven carrier sheet and a pair of gatherable nonwoven facing sheets easily less stretchable than the carrier sheet, sandwiching the carrier sheet between the facing sheets while the carrier sheet is in a partially stretched condition and autogenously bonding the facing sheets together through the carrier sheet at spaced apart sites thereby simultaneously forming breathable apertures in the carrier sheet while laminating the carrier and facing sheets together at the spaced apart sites.

In another aspect of the present method, the carrier sheet may be bonded to at least a pair of creped facing sheets which are extensible when the film carrier is stretched. Further the method may be performed with a combination of creped facing sheets and a partially stretched carrier sheet.

In another aspect of the instant invention, the elastomeric laminar fabric produced by the present method may be incorporated into a personal absorbent article such as a diaper outer cover material or elastic leg and waist gathers.

In a further aspect of the instant invention, the nonwoven laminar fabric is incorporated as an outer cover or as waist gathers in a personal absorbent article.

An advantage of the instant invention is the simultaneous formation of an elastic breathable laminar fabric without adhesives from a liquid impermeable elastic carrier sheet sandwiched and bonded between nonwoven facing sheets.

Another advantage of the instant invention is enhanced elastomeric properties of the laminate.

Another advantage is the elimination of the need for handling a tacky adhesive material during the laminating and converting processes.

Another advantage of the instant invention is the provision of inexpensive soft fabric gathers which cooperate with a resiliently stretchable outer cover to maintain an absorbent insert in conforming registration with the body for absorbing and containing body wastes.

A further advantage of the instant invention is an enhanced comfort and feel as well as a self-adjusting fit of the garment while presenting a smooth aesthetically pleasing external appearance when worn.

BRIEF DESCRIPTION OF THE DRAWINGS

FIG. 2A is a sectional view of cross-section 2A—2A of FIG. 2;

FIG. 2B is a sectional view of cross-section 2B—2B of FIG. 2;

FIG. 3A is a sectional view of cross-section 3A—3A of FIG. 3;

FIG. 12 is a partial plan view of the invention;

FIG. 13 is a sequential view of FIG. 12;

DETAILED DESCRIPTION OF THE PREFERRED EMBODIMENTS

Figure 1:
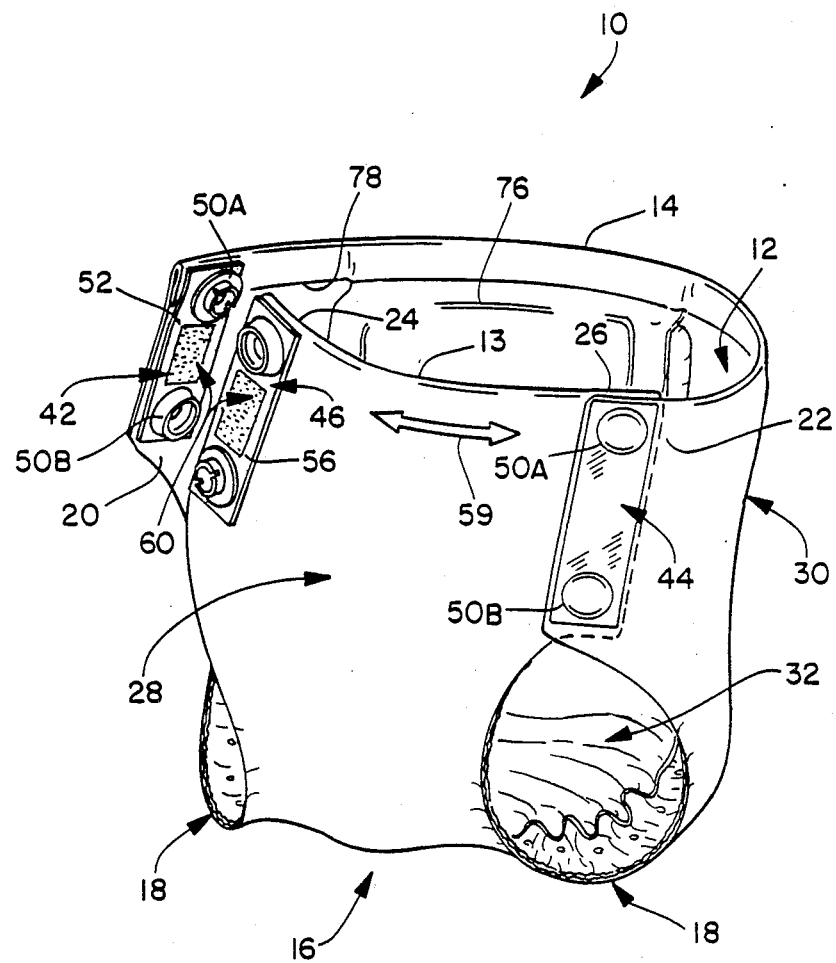
FIG. 1 is a perspective view of the invention.

Referring to FIG. 1, according to the instant invention, there is provided a disposable absorbent garment, generally shown at 10, such as a disposable diaper, training pant or incontinent garment, comprising an outer cover, generally indicated at 12, including opposed front 13 and rear 14 waist sections together defining a waist opening. A crotch section, generally shown at 16, is situated between a pair of leg openings, generally indicated at 18, delimited along outermost portions of said crotch section 16 of the outer cover 12. Ear portions 20, 22, 24, 26 are delimited generally between the opposed waist sections 13, 14 and each of the marginal leg openings 18, respectively, with longitudinally opposed pairs of said ears 20, 24 and 22, 26 being engageable with one another about the body of a wearer, such as a baby. The outer cover 12 preferably comprises an air-permeable, i.e., "breathable", elastomeric nonwoven laminar fabric wherein an elastic nonwoven web is joined to one or more gatherable nonwoven webs. Preferably, the laminate is resiliently stretchable from about 20 to about 200 percent in an essentially cross-body direction 59. Also preferably, the outer cover 12 has a generally asymmetrical hourglass profile with the leg openings 18 cut out from the crotch section 16 thereof, defining a front panel 28 having a laterally opposed front pair of said ear portions 24, 26 in conjunction therewith and a rear panel 30, preferably larger in area than the front panel 28, having another laterally opposed rear pair of said ear portions 20, 22 in conjunction therewith. The front 28 and rear 30 panels are separated from one another by the crotch section 16 which is narrowed due to the converging leg cut-out openings 18.

Figure 2:
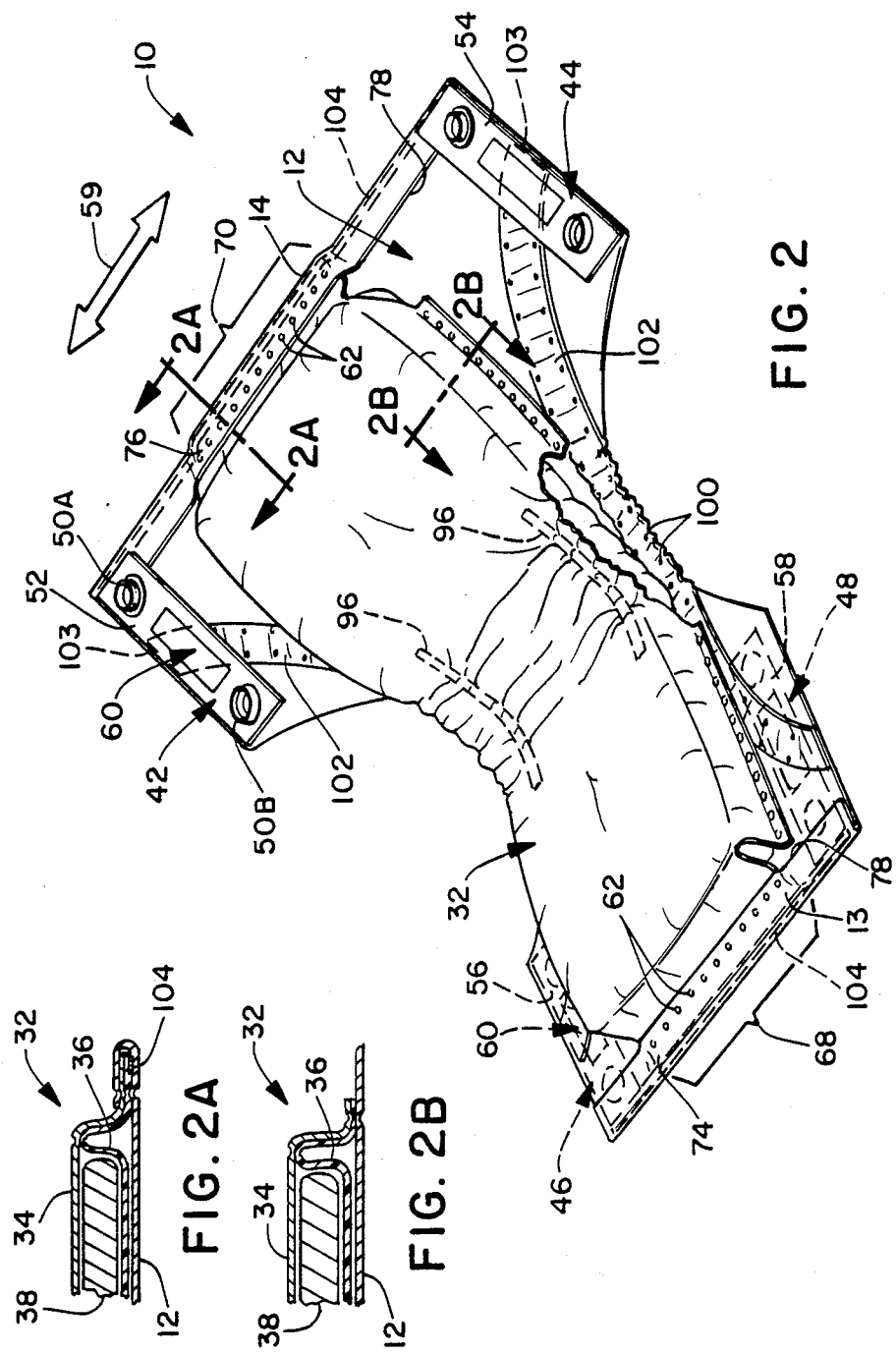
FIG. 2 is an internal perspective view of the invention.
Figure 3:
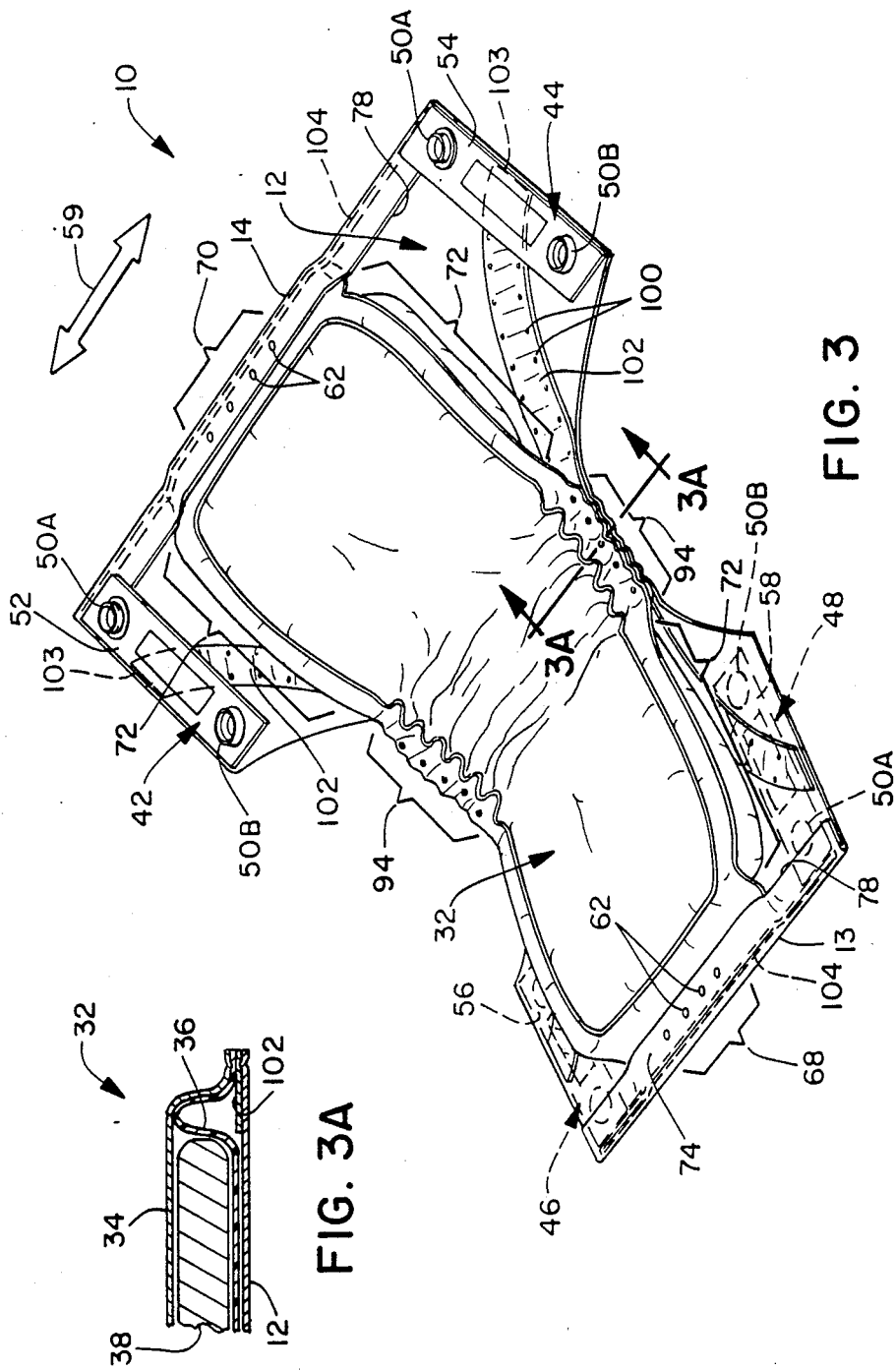
FIG. 3 is an internal perspective view of the invention.
Figure 4:
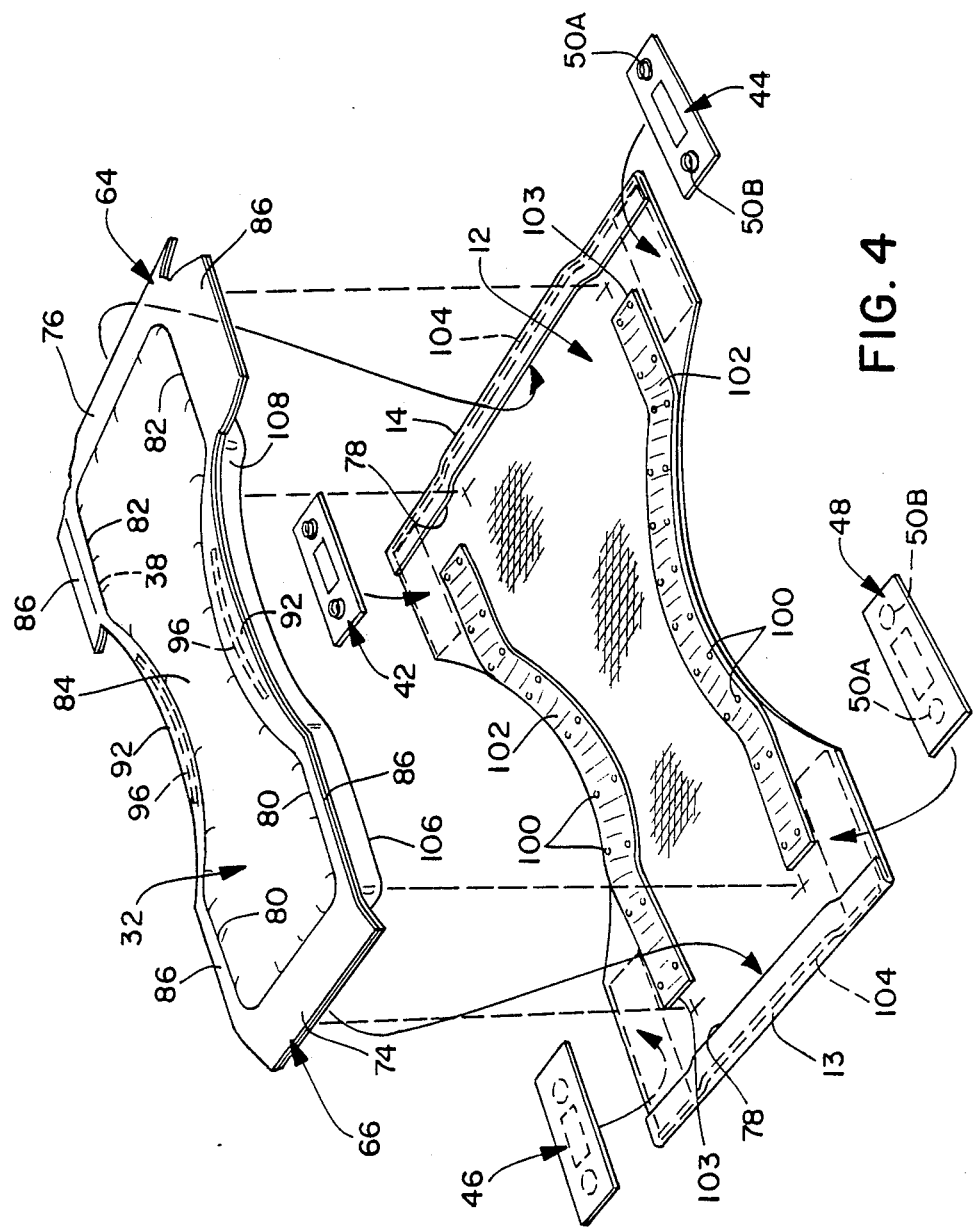
FIG. 4 is an exploded perspective view of FIG. 2.
Figure 5:
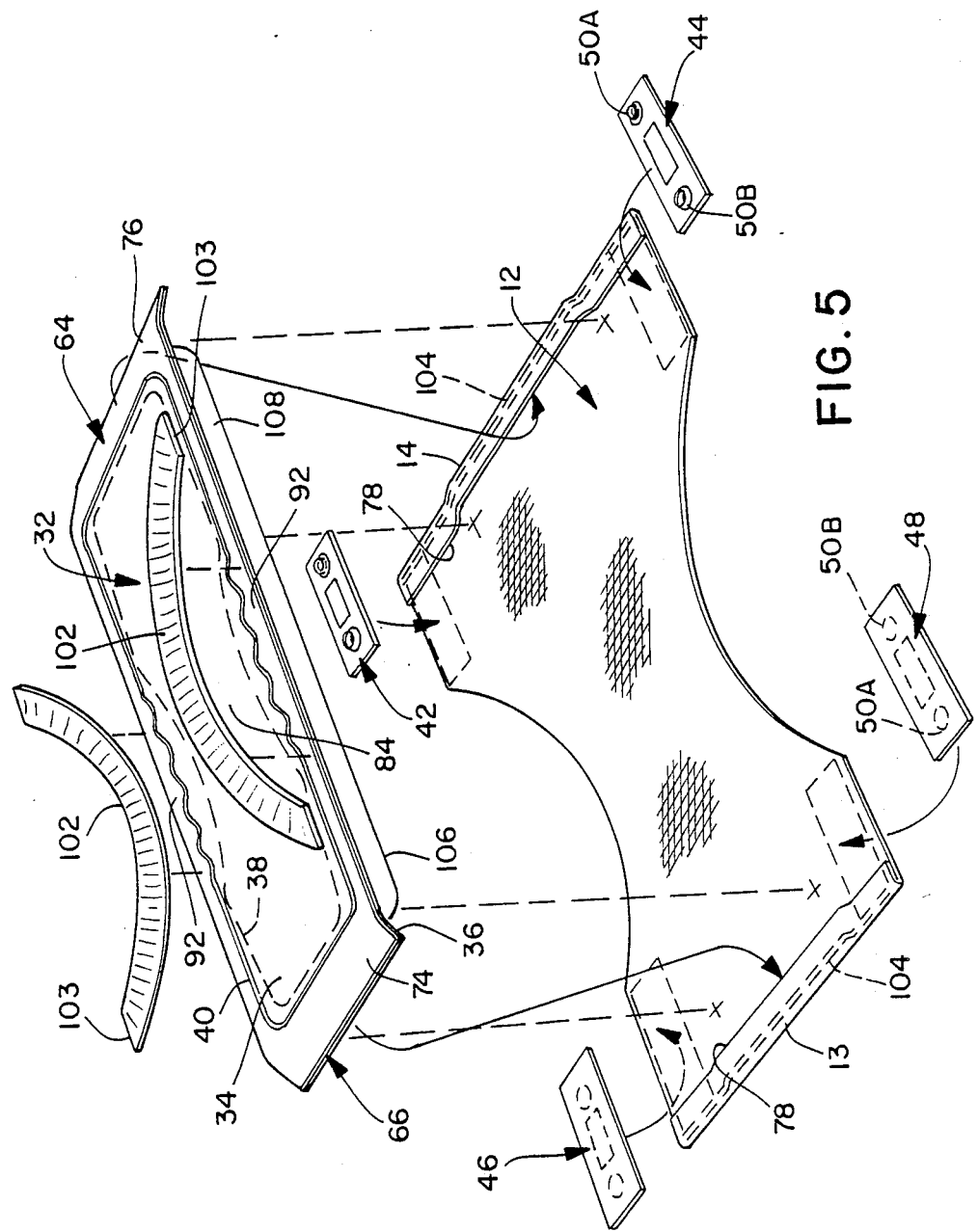
FIG. 5 is an exploded perspective view of FIG. 3.
Figures 6, 7:
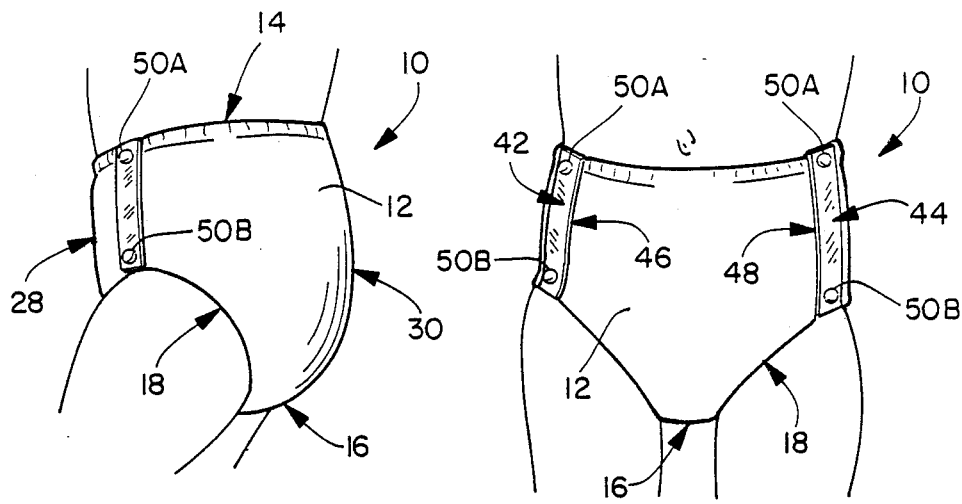
FIG. 6 is a side view of the disposable absorbent garment of the present invention shown secured around a baby.
FIG. 7 is a front view of the disposable absorbent garment of the present invention shown secured around a baby.

With reference to FIGS. 2, 3 and 4, an absorbent structure, generally indicated at 32, substantially superposable on the front 28 and rear 30 panels and the crotch section of the outer cover 12 for absorbing and containing bodily exudates, includes: a liquid-permeable bodyside liner 34, for example, a commercially available pattern-bonded, spunbonded polypropylene web; a liquid-impervious barrier 36, for example, a commercially available plastic film of polypropylene or the like; and an absorbent composite 38 disposed therebetween. The absorbent structure 32 is in the form of a separate insert, typically of substantially nonstretchable materials, integrated into the resiliently stretchable outer cover 12 whereby the functional stretchability of the outer cover is substantially unrestricted; however, the insert could also incorporate stretchable materials. As shown in FIG. 5, a preferably continuous ultrasonic or thermal bond 40. secures the absorbent structure 32 together by bonding the liner 34 and barrier 36 peripherally to one another about the absorbent core 38 disposed therebetween. It is important that the materials of the barrier 36 and liner 34 be compatible for autogenous bonding; accordingly, polypropylene has been found to be suitable for both the liner and barrier material.

Referring to FIGS. 1 and 2, the garment 10 further comprises a plurality of full-length fastener members 42, 44, 46, 48 affixed generally longitudinally across the ear portions 20, 22, 24, 26, respectively, wherein longitudinally-opposed pairs 42, 46 and 44, 48 of said fastener members situated on corresponding longitudinally opposed ears 20, 24; 22, 26 are releasably engageable with one another about the body of a wearer to form substantially full-length closures from the waist to each of the leg openings 18. The rear fastener members 42, 44 each comprise fixed-position fastening means, specifically upper 50A and lower 50B snap elements longitudinally spaced from one another in essentially coplanar relationship and releasably engageable with mating snap elements 50A, 50B similarly situated on longitudinally opposed front fastener members 46, 48 (FIG. 1), forming upper 50A—50A and lower 50B—50B primary load-bearing closures. The snap pattern on each fastener member may comprise alternating spaced male and female snaps or cooperating pairs of spaced male or female snaps may lie on longitudinally opposed pairs of fastener members 42, 46 and 44, 48 which have mating sets of snap elements. Each pair of upper 50A—50A and lower 50B—50B primary snap closures are separated by opposed cooperating abutment surfaces 52, 56 and 54, 58, presenting secondary load-bearing closure means 60 for effecting and maintaining a substantially continuous secondary closure between the above-described primary snap closures when longitudinally opposed pairs 42, 46 and 44, 48 of said fastener members are fastened together, providing full-length, non-collapsible, fixed-point fastening of the garment substantially from waist to leg of the baby. The full-length closures provide dimensional integrity to the resiliently stretchable garment during the various and often extreme bodily movements and positions of the wearer, such as a diapered baby. The diaper does not gap or collapse at the hip and waist regions, instead being form-fitting and generally self-adjusting, unlike the prior art. The secondary load-bearing closure means 60 may take various forms, for example: an intermediate third snap; a strip of cohesive material obtained by treating a substrate material with an adhesive having greater affinity for itself than for other materials, satisfactory adhesive materials for this purpose being NIP-WELD TM Nos. 2082-939 and 2132-939, manufactured by Findlay Adhesive Corporation, Milwaukee, Wisc.; a hook and loop material wherein the hook and loop portions of a tape material such as Velcro ® (a trademark of Velcro, USA) are respectively secured in strips on longitudinally opposed fastener members 42, 46 and 44, 48, preferably with the softer loop portion on the surface of the ear portion facing the skin, thus avoiding possible incidental skin contact with the abrasive hook portion. The fastener members may be constructed from a 2.0 oz/yd$^2$ spunbond substrate sheet cut into generally rectangular-shaped strips having the primary upper and lower spaced snap closures staked onto the strip as is known in the art. The snap elements may be of a metal or plastic material, for example, polyacetal or polypropylene. The fastening pattern is preferably arranged so that the snaps on the laterally 42, 44; 46, 48, as well as longitudinally 42, 46; 44, 48 opposed fastener members are fastenable with one another. As a result, a preferred method for disposal of the soiled garment upon removal from the body is easily accomplished by folding and rolling the front panel 28 inwardly over the waste containing surface and then fastening the rear pair of fastener members 42, 44 to one another thereby neatly bundling the garment into a closed compact package for disposal.

With reference to FIG. 2, the laterally opposed rear fastener members 42, 44 are shown fixedly attached across the bodyside of the rear pair of ears 20, 22, while the other pair of laterally opposed fastener members 46, 48 are affixed to the externally facing side of the front pair of ears 24, 26, for releasable engagement of the rear pair of fastener members 42, 44 in overlying relationship with the front pair of fastener members 46, 48. Alternatively, the front pair of fastener members 46, 48 may be affixed to the body facing surface of the front pair of ears 24, 26 and the rear pair of fastener members 42, 44 affixed to the external facing surface of the rear pair of ears, for releasable engagement of the front pair of fastener members 46, 48 in overlying relationship with the rear pair of fastener members 42, 44, depending upon the particular fastening pattern desired. The waist sections 13, 14 of the outer cover 12 have the insert 32 integrated thereinto according to the present invention as will be set forth more fully below.

It is important to minimize the number of bonds and total bond area used in integrating the absorbent insert to the outer cover or, where forming waist hems, the number of bonds used to bond the outer cover to itself. The Applicants have discovered that the number of bonds correspondingly affects the stretch elongation in the elastomeric component that is bonded. Not only does a lesser number of bonds result in less stretch loss, but the greater the spacing apart of bond points, the less stretch elongation is affected. Accordingly, bonding patterns should be selected that significantly reduce the amount of stretch lost by means of the density and spacing of the bond points. Specifically, the fewer the bonds integrating the insert along the waist sections, the less stretch is inhibited in said waist sections. Similarly, where the insert is integrated at the crotch section as discussed below with reference to FIG. 3, the less stretchability is inhibited about the leg openings.

The garment of the present invention is directed toward an integration means for integrating an absorbent insert structure, typically of non-stretchable material, into a relatively stretchable elastomeric outer cover while allowing substantially unrestricted functional stretchability thereof, thereby holding said insert in registration with the body of a wearer while maintaining the total garment anatomically form-fitting and generally self-adjusting. These objectives are preferably addressed while utilizing the full-length, fixed position fastening system elucidated above in combination with the features described hereinafter with reference to FIGS. 2–5 and 10–15.

The instant garment 10 is constructed and assembled as shown by FIGS. 2–5. The anatomically form-fitting, generally self-adjusting disposable absorbent garment of the instant invention comprises the above-described breathable elastomeric outer cover 12. Attachment means, such as the bonds 62, are provided for attaching and integrating the opposed longitudinal ends 64, 66 of said absorbent insert 32 to said outer cover 12 at selected front 68 and rear 70 waist attachment zones along said front 13 and rear 14 waist sections, respectively, defining one or more free-span zones 72 underlying said insert 32 wherein the functional stretchability of said outer cover in said free-span zone 72 is substantially unrestricted. It will be understood that where the insert 32 is integrated only at the waist attachment zones 68, 70, the free-span zone underlies the entire longitudinal length of the absorbent insert 32. Significantly, those portions of the waist sections not included in the waist attachment zones 68, 70 are, nevertheless, included in the free-span zone 72. It will also be understood that the insert 32 may be adequately held by the outer cover in registration with the body without additional bonding in the free-span zone 72 of the front 28 or rear 30 panels or the crotch section 16; however, additional elastication or bonding in other areas of the outer cover and absorbent insert may be provided for further contour and fit, as will be detailed below with reference to FIGS. 2–5. Although the free-span zones 72 can be provided in either or both of the front 28 and rear 30 panels, it is the stretch properties of the rear panel 30, which is preferably larger than the front panel 28, that are more important, especially when the fastening pattern to be employed is back-over-front, that is, when the rear pair of laterally opposed fastener members 42, 44 are brought around the body in overlying relationship with the front pair of laterally opposed fastener members 46, 48, respectively, to fasten the garment 10 about a wearer. It should be noted, that cross-body stretch in the crotch section 16 of the outer cover 12 during use is minimally required so that bonding of the insert at the leg openings 18 of the crotch section does not significantly affect cross-body functional stretch properties of the outer cover. The outer cover 12, among other functions, primarily holds the insert 32 in proper bodily registration and, unlike the prior art, does not itself need to provide a waste containment barrier.

The absorbent insert further comprises at least one but preferably front 74 and rear 76 waist attachment flaps respectively situated at the opposed longitudinal ends 66, 64 of the insert and extending from the liner 34 beyond the terminal ends of the absorbent composite 38 and attached or bonded to said front 13 and rear 14 waist sections, respectively, in said waist attachment zones 68, 70. The front 13 and rear 14 waist sections preferably each have finished hems 78 along the waist opening wherein the front 74 and rear 76 waist attachment flaps are entrapped and bonded within the hems 78 at said waist attachment zones 68, 70. The waist hems 78 comprise inwardly folded-over edges of outermost portions of said waist sections 13, 14 (FIGS. 4 and 5).

As shown in FIGS. 4 and 5, the absorbent composite 38 may have a generally hourglass shape, including opposed terminal ends past which the waist attachment flaps 74, 76 extend and front 80 and rear 82 pairs of marginal sides separated by a narrowed intermediate portion 84 having outermost sides thereof spaced inwardly from the leg openings 18 of the outer cover 12. With reference to FIGS. 2 and 4, the invention further comprises a pair of side attachment flaps 86 extending from said liner 34 beyond either of the front 80 and, preferably, the rear 82 marginal sides of the absorbent composite 38. As shown in FIGS. 2 and 4, a second pair of said side attachment flaps 86 may form extensions of the liner 34 beyond the opposed front marginal sides 80 of the absorbent composite 38. The side attachment flaps 86 are attached, preferably bonded, to either of the front 28 and rear 30 panels, deflecting laterally with the outer cover 12 when the outer cover 12 is stretched in the cross-body direction 59, thereby functionally maintaining the nonrestrictive free-span zone 72 while additionally supporting the insert 32 in registration with the body of a wearer. The side attachment flaps 86 preferably extend from the rear lateral sides 82 of the absorbent composite 38 which are superposed upon the rear panel 30, since stretch in the larger rear panel is more functionally significant than in the front panel 28. Both pairs of side flaps 86 can be used and, like the waist flaps 74, 76, may have diagonally cut corners, as shown in FIGS. 2–5, to reduce the amount of loose, unattached material in the free-span zones 72. Where the waist flaps 74, 74 comprise coextensions of the liner and barrier, it is preferable that they not be sealed together along the outermost peripheries of the waist flaps to allow the materials to slip past one another in the waist attachment zones during cross-body stretching; however, the perimeter bond 40 seals the liner and barrier together about the terminal ends of the absorbent composite 30 to prevent leakage therefrom.

Referring to FIGS. 10–15, either of the front 74 and rear 76 waist attachment flaps can include expansion means in the waist attachment zone 68, 70 for allowing cross-body expansion of the waist attachment flap 74, 76 when the outer cover 12 is stretched in the cross-body direction. Only the rear panel 30 of the diaper is shown in FIGS. 10–15 for illustrative purposes, since stretch in the rear panel is more critical, although it should be understood that expansion means may be preferably used in conjunction with both of the waist flaps. The expansion means may comprise one or more longitudinally extending expansible pleats (not shown), a plurality of longitudinally extending slits 88 (FIGS. 10–11), a plurality of notches 90 (FIGS. 12–13) or other expansible constructions, for example micro-creping (not shown). As shown by the sequential FIGS. 14 and 15, the expansion means may be retracted inwardly together and bonded along the waist attachment zones in such inwardly retracted position, allowing further expansion thereof when the outer cover 12 is stretched in the cross-body direction 59.

The expansion means may further optionally consist of an elastomeric waist flap comprising a contiguous stretchable liner, a stretchable elastomeric film barrier or both, bonded in the attachment zone. Elastomeric liner materials are taught by U.S. Pat. No. 4,013,816 to Sabee and elastomeric films by U.S. Pat. No. 4,418,123 to Bunnelle, et al.

With reference to FIGS. 2-5, particularly FIGS. 3 and 3A, the invention further comprises a pair of crotch flaps 92, extending from the liner 34 outwardly beyond laterally opposed sides of the intermediate portion 84 of the absorbent composite 38 which, in turn, is superposed upon the crotch section 16 of the outer cover. The crotch flaps 92 may be bonded along the leg openings 18 in selected crotch attachment zones 94 wherein the number and spacing of the bonds should be selected, as mentioned above, to minimize the loss of stretch along and across the crotch section 16. Optionally, the crotch flaps 92 have longitudinally extending crotch elastic members 96 applied thereon. As shown in FIG. 4, the crotch flaps 92 comprise extensions of either of said liner 34 and barrier 36, defining an elasticized contractible flap wherein the crotch elastic member 96 is applied to the crotch flap 92 in a partially stretched condition to gather the crotch flap about the perineal region of a wearer and, in combination with the outer cover 12, hold the insert in registration with the body. The crotch elastic members 96 may be spaced inwardly from the marginal edges of the intermediate portion 84 of the absorbent composite 38 or, preferably, outwardly therefrom a distance of at least 0.75 inches as measured from the marginal side of the absorbent composite 38 to the outer edge of the crotch elastic 96, thereby forming an elasticized contractible line extending longitudinally along and spaced outwardly from the marginal side of the intermediate portion 84 of the absorbent composite 38. The crotch flaps 92 need not function as attachment flaps (FIGS. 2 and 4) or they may be bonded or otherwise attached in the crotch attachment zones 94 along the leg openings.

According to the invention, therefore, either of the waist attachment flaps 74, 76 (FIG. 2A), side attachment flaps 86 (2B) and crotch attachment flaps 92 may comprise coextensions of the barrier 36 and liner 34 or may comprise either the barrier 36 or liner 34 alone. The flaps typically comprise materials that are not resiliently stretchable relative to the outer cover and need not be contiguous with the liner or barrier material.

The outer cover preferably has a generally asymmetrical hourglass shape wherein the leg openings 18 are formed by cutting out converging arcuate areas from the outer cover 12, defining a narrowed crotch portion 16. Elastic leg members 102, preferably comprising breathable elastomeric nonwoven laminar fabric strips, extend along outermost portions of either of said leg openings 18 and said waist sections 13, 14 on the internal bodyside surface of the outer cover 12. Although the waist sections 13, 14 are shown here with waist elastic members 104 of, e.g. extruded film within the finished waist hems 78, an elastomeric nonwoven laminar fabric strip of the present invention could instead be applied along outermost portions of the waist sections 13, 14. Either of the leg 102 and waist 104 elastics can be attached at their innermost edges to the outermost edges of the leg openings 18 (not shown) or preferably, the strips 102 can be positioned in overlying relationship with the leg openings 108 so that the outermost edges of the strips coincide with the outermost edges of the leg openings 18 as shown in FIGS. 2, 3 and 3A. The laminar fabric comprising either of the leg 102 and waist 104, elastic members and the outer cover 12 may be formed of elastomeric fabric laminates taught herein.

Figure 16:
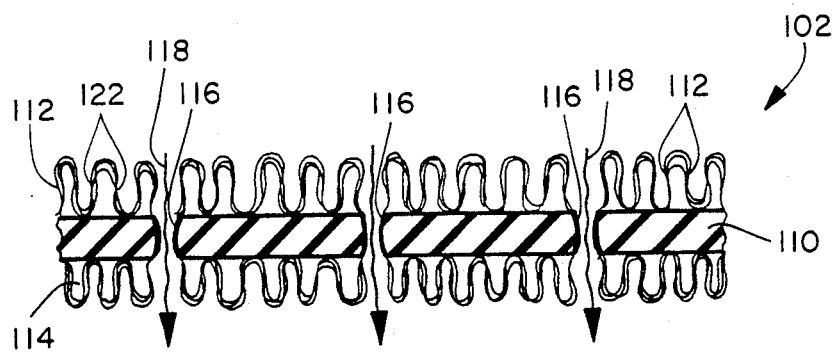
FIG. 16 is a side elevational view of the invention.
Figure 17:
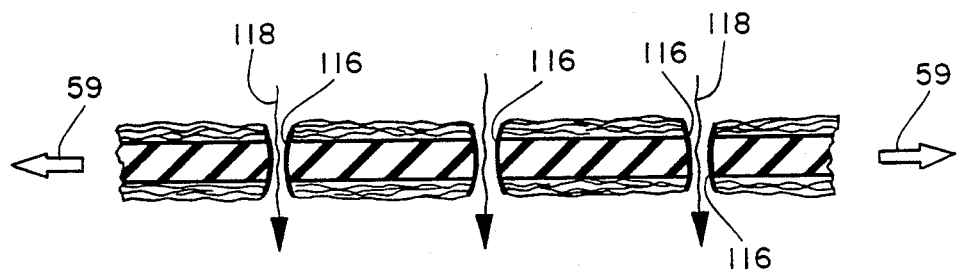
FIG. 17 is a side elevational view of the invention.
Figure 18:
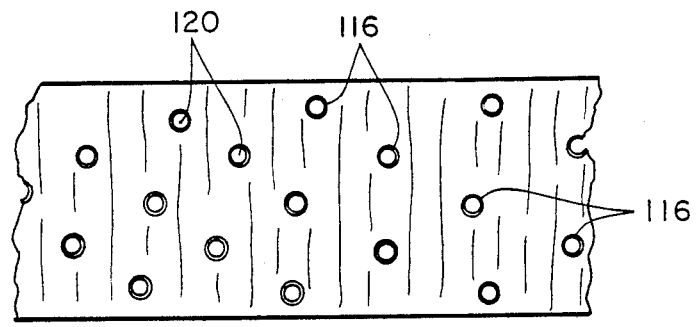
FIG. 18 is a top plan view of the invention.

With reference to FIGS. 16-18, there is shown the laminar fabric preferably comprising the leg 102 and optionally the waist 104 elastic members shown in the drawings. The preferred laminate for the leg elastics 102, and optionally the waist elastics 104, may also be used as the material for the outer cover 12; conversely the other preferred outer cover nonwoven laminates, discussed herein, may also be used as the leg or waist gathers. A method for making such a breathable cloth-like elastic nonwoven laminar fabric comprises the steps of sandwiching a liquid impermeable and nonself-adhering elastomeric film or nonwoven carrier sheet 110 between at least a pair of nonwoven facing sheets 112, 114 and bonding the facing sheets 114 together by autogenous bonds, shown by the arrows 118, such as ultrasonically or thermally-generated bonds, through the carrier sheet 112 at spaced apart sites 116, thereby forming breathable apertures 120 through the carrier sheet which laminate the carrier and facing sheets together at the spaced apart sites 116. As shown by FIG. 17, the carrier 112 and facing sheets 114 can be bonded together while the carrier sheet is stretched in a crossbody direction 59 or, as shown by FIG. 16, the carrier sheet can be sandwiched between a pair of creped or microcreped nonwoven facing sheets while the carrier sheet is in an unstretched or a partially stretched condition so that the facing sheets are expansible when the web is stretched. The advantage of bonding the nonadhesive elastomeric film carrier to the facing sheets while the carrier sheet is substantially unstretched or minutely stretched is that thermal or ultrasonic bonding can erode or even cause a heat set in the elastic carrier sheet, affecting the elastomeric properties thereof; further, eliminating the need for adhesive lamination avoids the complicated problems of stretching adhesives. As taught by the invention, the number and spacings of bonds 116 which are generated by a thermal or ultrasonic source 118, in the elastomeric film carrier sheet 110 further affects the stretch properties of the laminate 102 formed; moreover, these elastomeric properties are typically adversely affected when elastomeric film carriers are bonded to nonwoven facing sheets while the elastomeric material is stretched. The thermal or ultrasonically generated bonds 116 of the invention should be of sufficient strength to bond the facing sheets 112, 114 together through the 1 elastomeric film 110 while simultaneously creating breathable apertures 118 through the film 110. Further, the instant laminate 102 need not also be liquid impermeable, since neither the leg 102 nor waist elastic members nor the outer cover need to function as a waste containment barrier. For this purpose, many commercially available ultrasonic bonding apparatus, such as those produced by Branson Sonic Power Corporation of Danbury, Conn, can be suitably adapted by those skilled in the art to make the laminate. The facing sheets 112, 114 can be provided with minute pleats or folds 122 (FIG. 16) by commercially available processes of Micrex Corporation of Boston, Mass., commonly referred to in the art as "microcreping" wherein the length of the nonwoven facing sheets 112, 114 can be effectively reduced from about 20% to about 300% prior to bonding of the facing sheets 112 together through the carrier sheet, thereby enhancing the elastomeric properties of the carrier sheet as referred to above. A further consideration is that self-adhering elastomeric films, for example FULLASTIC®, a trademarked material manufactured by H. B. Fuller Co. of Minneapolis, Minn., experience variability in their combined elastomeric and adhesive properties when used with nonwoven fabric materials. Non-tacky materials are also easier to handle during the process. The laminar fabric produced by the above process may comprise facing sheets, 112, 114 of available spun-bonded, carded, spun-laced, airlaid, costructured or meltblown webs. Suitable extruded nonself-adhering elastomeric films for this purpose are manufactured by Deerfield Corporation of Deerfield, Mass. and J. P. Stevens Co. of East Hampton, Mass. Other microporous elastic films or meltblown elastic webs can be used as the elastomeric carrier sheet in the laminate.

Another method taught herein relates to the preferred outer cover laminate, which comprises a stretched elastomeric nonwoven carrier sheet bonded between nonwoven facing sheets. The carrier sheet further comprises a meltblown elastomer, preferably an A-B-A' block copolymer such as the Kraton® Series manufactured by Shell, and a co-extrudable polyolefin material, for example, polyethylene or polypropylene. The stretched carrier sheet and facing sheets are then passed together through a hot nip roll and bonded together. Typically, this laminate is breathable without separate apertures being formed therein, as is usually necessary with the laminar gathers described above. The leg elastics 102 have different stretch requirements, i.e. 0–300%, than the outer cover 12, e.g. 20–200%, and it has been found that the above-described method of using an extrudable nonself-adhering elastomeric film carrier sheet is preferred for the leg gathers 102. The pair of leg elastics 102 supplement the elastomeric outer cover and are operatively tensioned relative thereto, extending along the inner surface of the outermost portions of the leg openings 18, forming supplemental leg elastics 102 providing cushioned, cloth-like gathering of the garment 10 about the body of the wearer.

U.S. patent application Ser. No. 773,746, filed Sept. 6, 1985 and assigned to the instant assignee, discloses a stretchable outer cover with hemmed leg openings and elastics, for example FULLASTIC® or TUFTANE®, trademarked extruded elastic film materials, in the leg hems. The laminar fabrics of the present application extend along the internal peripheries of the leg openings, rather than within hems as is taught by the prior application listed immediately above.

In accordance with another aspect of the present invention, shown in FIGS. 2–5, the leg elastics 102, which may be formed from the above-described elastic composites, or simply from extruded films, such as FULLASTIC®, are routed so that each leg elastic 102 extends between opposed terminal ends 103 which are respectively placed adjacent the longitudinally opposed secondary closures 60 to gather the garment 10 about a wearer while directing tensile stresses away from the lower primary snap closures 50B—50B adjacent said leg openings 18 thereby reducing stress concentrations associated with said leg openings (FIG. 2). Further, the opposed terminal ends 103 of the leg elastics 102 may be affixed or anchored below the cooperating secondary closures 60 of the longitudinally opposed cooperating fastener members 42, 46 and 44, 48 (FIG. 4). The terminal ends 103 underlying the fastener members may be rendered inelastic by perforation or heat inactivation for ease of assembly and to avoid placing further stress on each fastener area. As a result, when the fastener members are fastened together about a wearer, the terminal ends 103 of each of the leg elastic members 102 are substantially juxtaposed, directing opposed substantially equivalent tensile forces from each leg elastic member against one another. The resultant balancing of torsional forces on the fastener members inhibits deflection of the fastener members outside a plane generally parallel to the surface of the body. It has been found that where there is an imbalance in tensile forces applied to the fastener members, a net torsional strain results causing the fastener members to angularly deflect which can lead to irritation and red marking of the skin. Accordingly, the above-described leg elastic 102 placement routes the tensile stresses thereof away from the front curvature of the wearer's leg adjacent the lower primary snap closures 50B—50B, instead directing them upwardly toward the upper hip region of the wearer adjacent the engaged secondary closures 60, more freely allowing hinged movement of the wearer's legs by distributing the elastic tensile stresses from an area overlying body surfaces requiring greater degrees of movement to an area of the garment overlying relatively flat body surfaces which experience lesser movement. The leg elastics 102 preferably are tensioned only in the outermost portions of the leg openings 18 corresponding to the inner thighs of a wearer and, in fact, may be applied to that portion of the leg openings with effectiveness in minimizing skin red marking of the thighs.

As can be seen in FIGS. 4 and 5, the barrier 36 closely surrounds the bottom 106, and sides 108 of the absorbent composite 38 (shown in phantom in FIG. 5) with the liner 34, extending across and contacting the top surface of the absorbent composite 38, imparting a generally rectangular boat-shaped configuration to the insert 32. The bottom 106 of the barrier 36 may include one or more relaxed localized areas adjacent the bottom of the absorbent composite 38 to accommodate swelling of the composite during use with, for example, a hydrogel material. The liner 34 and barrier 36 are bonded together substantially around the absorbent composite 38 by the perimeter bond 40, which may comprise either closely-spaced intermittent bonds or, preferably, a continuous autogenous bond.

Referring to FIGS. 3 and 5, the crotch attachment zones 94, wherein the crotch attachment flaps 92 are bonded, each comprise at least one but preferably about three discrete bonds at spaced apart locations within a linear distance of about 3.5 but less than 4 inches. The waist attachment zones 68, 70 comprise at least one but preferably about three discrete bonds 62 at spaced apart locations within a linear distance of about 1 inch. The leg elastic members 102 function cooperably with the stretchable outer cover for gathering the leg openings 18 about the wearer and can be applied in varying tensions relative thereto by adhesive, autogenous or pressure bonding.

Significantly, the absorbent structure 32 may be integrated into the outer cover 12 in the waist 68, 70 and crotch 94 attachment zones while the outer cover is stretched in the cross-body direction 59. The longitudinal length of the free-span zone 72 in the front 28 and rear 30 panels is preferably at least about 2.5 inches or the longitudinal length of the fasteners 42, 44, 46, 48. When the prestretched outer cover 12 is relaxed following attachment of the insert 32, the side attachment flaps 86, shown in FIGS. 2 and 4, retract inwardly underneath the absorbent composite 38. As with the leg elastic members 102, the waist elastic members 104 can also be similarly applied to the waist sections 13, 14 in a tensioned condition relative to the outer cover. Preferably, the distance between the outermost edges of the waist elastic member 104 and the longitudinal end of the absorbent composite is at least 0.75 inches at any given point. The crotch elastic members 96 may be attached to the liner 34, the barrier 36 or both the liner 34 and the barrier 36, depending upon the construction of the crotch flap 92.. Referring to FIGS. 3 and 5, the perimeter bond 40 may be undulatory along the intermediate portion 84 of the composite 38, imparting a scalloped edge and greater flexibility in the crotch region of the garment.

A preferred method of integrating an absorbent insert structure 32 into a resiliently stretchable nonwoven outer cover 12 and assembling a disposable absorbent garment comprises the steps of providing the outer cover with opposed front 13 and rear 14 waist sections, a central crotch section 16 and front 28 and rear 30 panels separated by the crotch and the waist sections, respectively, preferably prestretching the outer cover more than about 20% in a cross-body direction 59 parallel to the waist sections, superposing the insert 32 upon an inner surface of the outer cover, attaching longitudinally opposed ends 64, 66 of the insert to the waist sections in selected waist attachment zones 68, 70, respectively, defining free-span zones 72 allowing substantially unrestricted functional stretchability of the outer cover underlying the free-span zones 72. One aspect of the present integration method comprises the step of inwardly folding over the outermost edges of the waist sections 13, 14 forming waist hems 78 entrapping the longitudinally opposed ends 64, 66 of the absorbent insert therein and bonding the opposed ends 64, 66 of the insert within the waist hems 78 at the waist attachment zones 68, 70. Another aspect of the method attaches the insert to the outer cover using snaps (not shown), either while prestretching the outer cover prior to attachment or by situating the snaps on expansible or elastomeric waist attachment flaps, 74, 76 extending from the opposed longitudinal ends 64, 66 of the insert in the waist attachment zones. The instant method further comprises the step of applying elastomeric leg gathers 102 preferably of a breathable laminar fabric, along the leg openings 18.

A preferred method of using a disposable absorbent garment 10, comprises the steps of providing an outer cover 12 that is resiliently stretchable in an essentially cross-body direction with opposed fastenable front 13 and rear 14 waist sections, a central crotch section 16 and front 28 and rear 30 panels separated by the crotch 16, providing breathable elastomeric laminar fabric leg gathers 102 along the leg openings 18, providing an absorbent insert structure 32 having opposed longitudinal ends 64, 66 and substantially superposable on the cover 12 for absorbing and containing body exudates. The cover 12 is then stretched from about 20% to about 200% in the cross-body direction 59 while the insert 32 is superposed upon an inner surface thereof, then the opposed longitudinal ends 64, 66 of the insert 32 are attached along the waist sections 13, 14 in selected waist attachment zones 68, 70, defining free-span zones 72 allowing substantially unrestricted functional stretchability of the cover 12 underlying the free-span zones 72. The garment is then positioned underneath the lower torso of a baby and the waist sections fastened about the body. The method may further comprise the step of providing refastenable snaps (not shown), attaching the longitudinal ends 64, 66 of the insert 32 at the waist attachment zones 68, 70 wherein the snaps are fastened to a pre-stretched outer cover or situated on expansible waist attachment flaps 74, 76 situated at the opposed longitudinal ends 64, 66 of the insert 32.

With respect to the physical properties required of the fastening system, it has been found that the primary snap closure should have a peel strength of from about 600 grams to about 2,500 grams. Snaps having different opening strengths were evaluated in actual diaper wear studies wherein the minimum snap strength remaining fastened during an overnight wear period was found to be greater than 600 grams, while the maximum snap strength at which it was difficult to either manually engage or disengage the snap elements was found to be approximately 2,500 grams. The maximum peel strength allowable for the snap closure is further dependent on the material to which the snap is staked or otherwise secured and the ability or strength of the user, such as a parent, to open the snap. Snap strengths were quantitatively determined by a 180° peel test performed at 4.0 inches per minute. The minimal strength requirement for the secondary closure is essentially dependent upon shear strength rather than peel strength, provided that torsional strain on the fastener member is minimized. Hook and loop materials of varying peel and shear strengths were tested, and a direct correlation found between shear strength and functionality. The minimum shear strength allowing for successful overnight wearing of the diaper was greater than about 3,750 grams per square inch. The maximum shear strength of the secondary closure is itself not critical, rather it is dependent upon the maximum shear strength for the primary snap closure. Materials were tested by a shear test wherein a sample size of bonded area, e.g. cohesive adhesive or Velcro ®, of one square inch was pulled at 4.0 inches per minute.

With respect to the dimensions of the particular elements of the fastener member, it has been found that the diameter of the snap element preferably should not exceed 0.4 inches and that the ratio of the snap diameter to the minimum distance separating the snaps is preferably less than 6, expressed mathematically:

$$D/d < 6$$

where $D$ = maximum diameter of snap
and $d$ = minimum distance separating the respective rims of the snaps Further, it has been found that the thickness or outwardly projecting height of the snap elements 50A and 50B is preferably from about 0.01 to about 0.19 inches in order to minimize impingement upon the skin.

The instant fastening system preferably combines a hybrid of elements in cooperation with unique materials, while prior fastening systems attempting employ singular materials or elements unsuccessfully met the criteria of the instant system. The instant fastening system: maintains a substantially non-collapsible, full-length closure from waist to leg for diaper garments and the like, presenting a neat, trim garment-like appearance during wear with minimal sagging of the waist or gapping and blousing at the hips; provides a point-to-point fastening system easy to fasten and unfasten and refastenable at least five times; and provides a system that is safe to the wearer without sharp edges or materials which would irritate the skin. Another performance criterion met by the instant fastening system during wear is that the waist and leg areas of the fastener experience high shear and peel forces which the instant system can withstand while maintaining a sufficient rigidity to prevent the diaper from collapsing, that is, maintaining the integrity of its dimensional length. The fastening system comprises a strong durable fastening point via primary closures at the waist and leg portions of the fastener and a weaker secondary closure between the primary closures, each of the closures having peel and/or shear strengths which correspond to the forces placed on said closures during actual use.

FIGS. 6-9 show a disposable diaper 10 of the instant invention as it would be worn by a baby wherein the disposable diaper has a neat, trim fit and appearance when viewed from different perspectives.

Figures 8, 9:
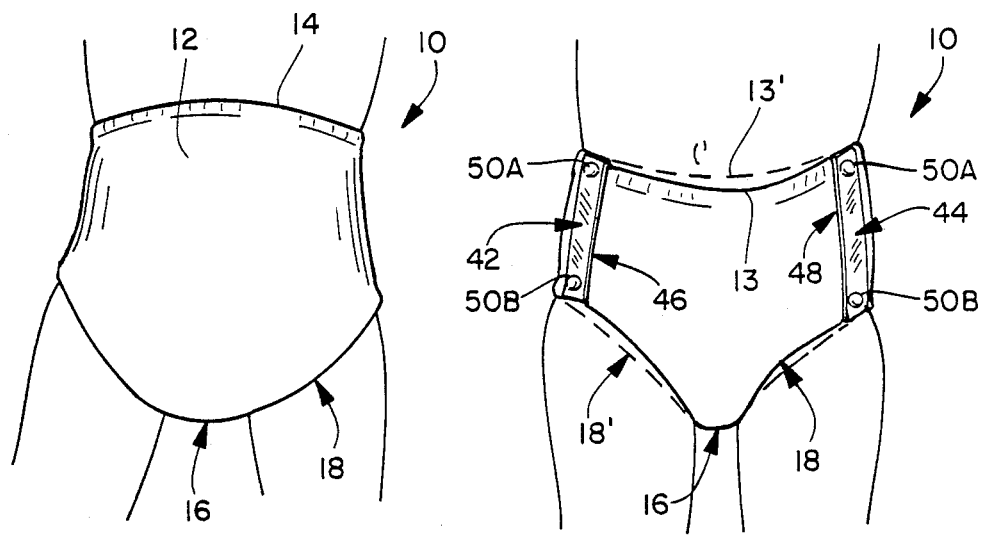
FIG. 8 is a back view of the disposable absorbent garment of the present invention shown secured around a baby.
FIG. 9 is a front view of the disposable absorbent garment of the present invention showing the disposition of the garment on the baby after being worn for a period of time.
Figure 10:
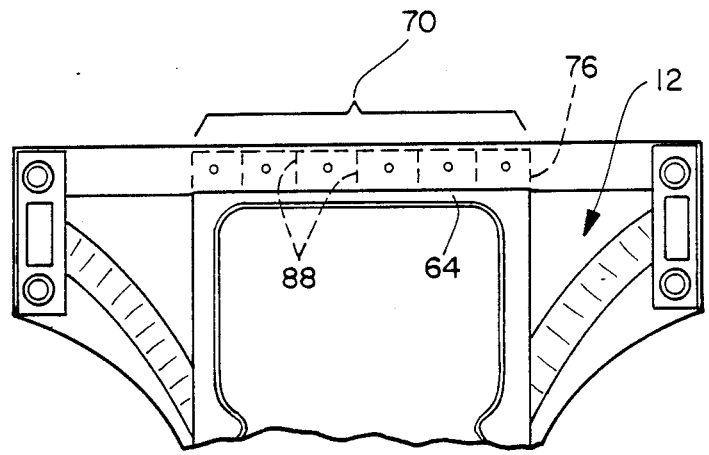
FIG. 10 is a partial plan view of the invention.
Figure 11:
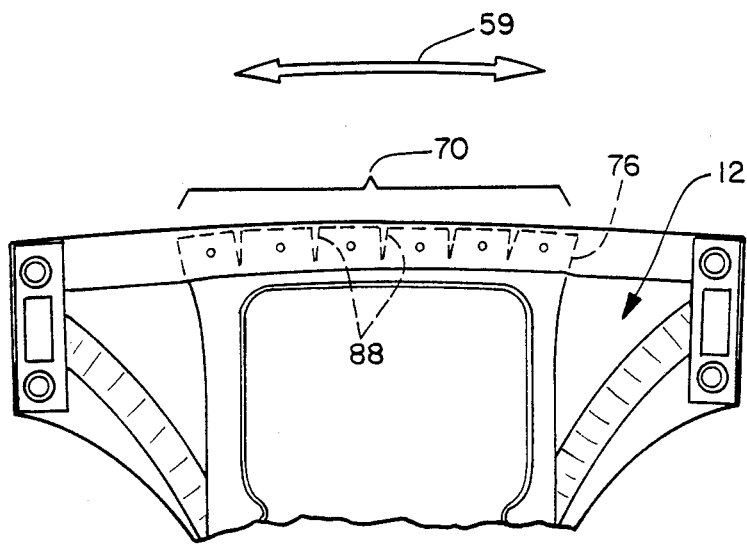
FIG. 11 is a sequential view of FIG. 10.
Figure 14:
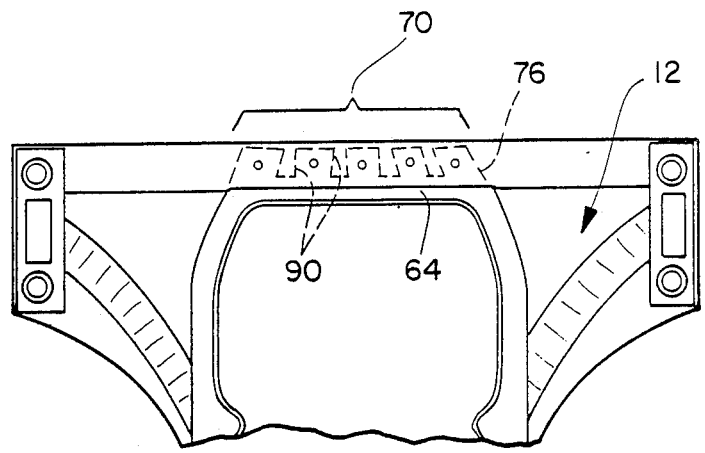
FIG. 14 is a partial plan view of the invention.
Figure 15:
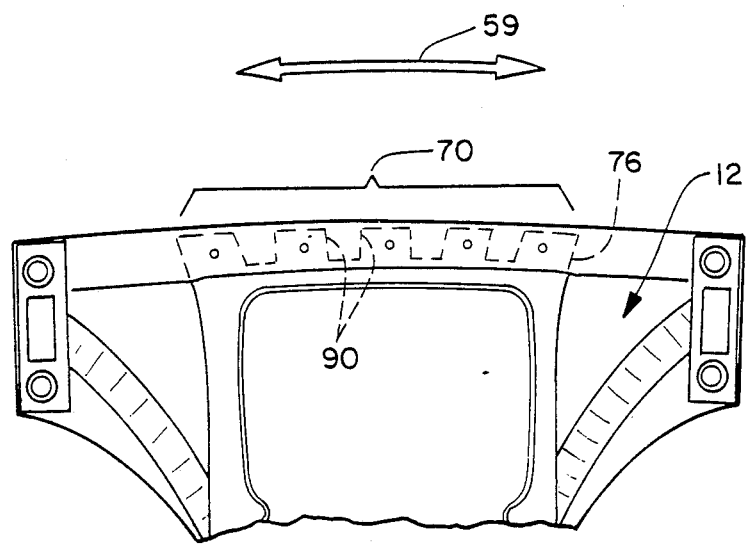
FIG. 15 is a sequential view f FIG. 14.

FIG. 9 illustrates the dimensional integrity of the diaper, as shown by the minimal extent the diaper moves or sags from an initial position as indicated by the dashed lines 18' and 13' after being worn by an infant for a period of time.

Although the stronger primary closures at the end points of each fastener member may be garment snaps, for example, a multi-component polyacetal snap, smaller snaps have been shown to be as effective; however, it is believed a large enough snap is desirable for easy fastening by the user. The specific snap elements shown are not the only embodiments that will produce the desired strong closure at leg and waist. There are several snap-like closures which could be equivalent within the scope of the present invention, for example, the male portion of the snap could be a single stud which is snapped through an aperture in a piece of film or nonwoven, functioning as the female portion of the snap set and having a slightly smaller diameter hole than the diameter of the stud, producing an economical snap. Further, the fastener members need not be previously secured on a separate substrate strip as shown wherein the strip is then bonded to the stretchable outer cover by autogenous bonding, for example, ultrasonic or thermal bonding, as in the instant invention. Multi-component snaps are available which are bondable or otherwise securable to a stretchable outer cover material of the type contemplated by the instant invention. An advantage of the instant system is that, due to the consumer's vast experience with snaps on infant clothing and the widespread use of Velcro® and similar materials, the fastener members are easily fastened; further, the automatic fastening of the secondary closure is effected when the two primary snap closures are made. The quantitative physical properties described above combine to define a fastening system quantitatively independent of the materials or type of mechanical fasteners employed; moreover, the resultant full-length, fixed-point fastening system produces a desirable fit and appearance.

A selection criterion for the selection of a material and design for fastener members 42, 44, 46, 48 is to consider the Moment of Inertia (I) of the material in conjunction with the Modulus of Elasticity (E). This selection criterion which involves the product of (E)(I) is utilized as follows. The value (E)(I) is determined in a material/design combination, that is, the value (E)(I) is determined for a particular fastener design utilizing a particular material. The value (E)(I) is calculated from the following formula taken from the textbook "Mechanical Engineering Design," 2nd Ed. by Joseph E. Shigley, Published by McGraw-Hill, 1972, page 699.

$$EI = L^3 M/48$$

wherein M is the slope of the tangent to the initial straight-line portion of the load-deflection curve of deflection as obtained from ASTM test D-790 and wherein L is the support span as defined by ASTM test D-790.

In order to reduce the problem of skin red-marking arising when a baby sits down and the fastener refuses to conform with the curves and folds of the body, the following have been found preferable. The fastener should have at least one area with a Modulus of Elasticity or stiffness of less than 0.1 pound-inches$^2$ with such areas separated by an area having a stiffness less than 0.1 pound-inches$^2$ and not greater than 0.4 inches in length. In other words, the diameter of the snap preferably should not exceed 0.4 inches. The ratio of the length of the area with stiffness greater than 0.1 to the length of the area with stiffness less than 0.1 should not exceed 6. Although the above and other criteria stated herein have been applied to the instant fastening system, the relationships would also directly apply to other forms of fastening systems such as zippers, buttons, clasps, etc., so that when these criteria are met, the fastener should be flexible enough to conform to the folds and creases in the body of a sitting, kneeling or crawling infant when the fastener is positioned on the diaper in the area shown in FIGS. 1, 2, 3 and 6-9.

Turning now to the outer cover 20 of the present invention, which is preferably made from a resiliently stretchable elastomeric nonwoven laminar material having a stretchability of from about 20 percent to about 200 percent. The term stretchability as used herein is defined by the following relationship:

stretchability=((final dimension—initial dimension)/initial dimension)×100%

Since the outer cover 20 is also resilient, the outer cover returns essentially to its initial dimension when the stretching force is removed.

One such resiliently stretchable material is disclosed in U.S. patent application Ser. No. 760,698 in the name of Tony J. Wisneski and Michael T. Morman, assigned to the assignee of the present application, entitled "Polyolefin-containing Extrudable Compositions and Methods for their Formation Into Elastomeric Products", the disclosure of which is incorporated herein by reference and relied upon. That application provides extrudable elastomeric compositions which, after extrusion, solidify to form elastomeric products such as, for example, fibrous nonwoven elastomeric webs. The extrudable elastomeric compositions are blends of (1) from at least about 10 percent, by weight, of an A-B-A' block copolymer, where "A" and "A'" are each a thermoplastic polymer endblock which includes a styrenic moiety such as a poly(vinyl arene) and where "B" is an elastomeric poly(ethylene-butylene) midblock, with (2) from greater than 0 percent, by weight, to about 90 percent, by weight, of a polyolefin which, when blended with the A-B-A' block copolymer and subjected to appropriate elevated pressure and elevated temperature conditions, is extrudable, in blended form, with the A-B-A' block copolymer. The A-B-A' block copolymer serves to impart elastomeric properties to products formed from the extrudable composition and the presence of the polyolefin in the blend serves to reduce the viscosity of the composition as compared to the viscosity of the neat, that is, pure, A-B-A' block copolymer and thus enhances the extrudability of the composition.

Preferably, the "A" and "A'" thermoplastic styrenic moiety containing endblocks of the block copolymer are selected from the group including polystyrene and polystyrene homologs such as, for example, poly(alpha-methylstyrene). In some embodiments the "A" and "A'" thermoplastic styrenic moiety containing endblocks are identical. Preferably, the polyolefin is selected from the group including at least one polymer selected from the group including polyethylene, polypropylene, polybutene, ethylene copolymers, propylene copolymers, butene copolymers or blends of two or more of these materials.

The blend usually includes from at least about 20 percent, by weight, to about 95 percent, by weight, of the block copolymer and from at least about 5 percent, by weight, to about 80 percent, by weight, of the polyolefin. For example, the blend may include from about 30 percent, by weight, to about 90 percent, by weight, of the block copolymer and from about 10 percent, by weight, to about 70 percent, by weight, of the polyolefin. Preferably, the blend includes from about 50 percent, by weight, to about 90 percent, by weight, of the block copolymer and from about 10 percent, by weight, to about 50 percent, by weight, of the polyolefin. For example, the blend may include from about 50 percent, by weight, to about 70 percent, by weight, of the block copolymer and from about 30 percent, by weight, to about 50 percent, by weight, of the polyolefin. One blend includes about 60 percent, by weight, of the polyolefin.

The extrudable composition is extruded or otherwise formed, such as, for example, by molding, for example, injection molding, at an appropriate, that is effective, combination of elevated pressure and elevated temperature conditions. These conditions will vary depending on the polyolefin utilized. For example, the extrudable composition should be extruded or otherwise formed at a temperature of at least about 125 degrees Centigrade if polyethylene is utilized as the polyolefin in the blend or at least about 175 degrees Centigrade if polypropylene is utilized in the blend, for example, at a temperature of from at least about 290 degrees Centigrade to about 345 degrees Centigrade, more specifically, at a temperature of from at least about 300 degrees Centigrade to about 335 degrees Centigrade, into elastomeric products such as, for example, elastomeric fibers, which may be collected as a fibrous nonwoven elastomeric web.

Preferably the blends are extrudable within the above-defined temperature ranges at elevated pressures within the die tip, (for example, within the extrusion capillaries of a die tip having thirty (30) extrusion capillaries per lineal inch of die tip with each of the capillaries having a diameter of 0.0145 inches and a length of 0.113 inches) of no more than about 300 pounds per square inch, gage, for example, from pressures of from about 20 pounds per square inch, gage, to about 250 pounds per square inch, gage. More specifically, the blends are extrudable within the above-defined temperature ranges at pressures of from about 50 pounds per square inch, gage, to about 250 pounds per square inch, gage, for example, from about 125 pounds per square inch, gage, to about 225 pounds per square inch, gage. Higher elevated pressures can be utilized with other die designs having a lower number of capillaries per inch of die, but, generally speaking, lower production rates result.

Importantly, it has been found that the extrudable compositions are extrudable at satisfactory throughput rates because the presence of the polyolefin in the extrudable composition reduces the viscosity of the extrudable composition, as compared to the viscosity of the neat, that is, pure, block copolymer, to satisfactory levels. This reduced viscosity proportionally reduces the die tip pressure if all other parameters remain the same. For example, the viscosity of the extrudable compositions will generally be less than about 500 poise when extruded at the above-defined elevated temperature and elevated pressure ranges. Preferably, the viscosity of the extrudable composition is less than about 300 poise when extruded at the above-defined elevated temperatures and elevated pressure ranges. For example, the viscosity of the extrudable composition may be from at least about 100 poise to about 200 poise when extruded at the above-identified elevated temperature and elevated pressure conditions.

Because the polyolefin reduces the viscosity of the blend, as compared to the viscosity of the block copolymer, the extrudable composition is extrudable within the above-identified elevated temperature and elevated pressure ranges, through a die tip having, for example, thirty capillaries per inch of die tip with the capillaries having a diameter of about 0.0145 inches and a length of about 0.113 inches at a rate of from at least about 0.02 grams per capillary per minute to about 1.7 or more grams per capillary per minute. For example, the extrudable composition may be extruded through the above-identified die tip having capillaries with a diameter of about 0.0145 inches and a length of about 0.113 inches at the rate of from at least about 0.1 grams per capillary per minute to about 1.25 grams per capillary per minute. Preferably, the extrudable composition is extrudable through the above-identified die tip having capillaries with a diameter of about 0.0145 inches and a length of about 0.113 inches at the rate of from at least about 0.3 grams per capillary per minute to about 1.1 grams per capillary per minute.

The extrudable composition may be formed into fibrous nonwoven elastomeric webs preferably having microfibers with an average diameter of not greater than about 100 microns, and preferably having an average basis weight of not more than about 300 grams per square meter, for example, an average basis weight of from about 5 grams per square meter to about 100 grams or more per square meter. More specifically, an average basis weight of from about 10 grams per square meter to about 75 grams per square meter. For example, a fibrous nonwoven elastomeric web may be formed by extruding the extrudable composition at an appropriate, that is, effective, combination of elevated temperature and elevated pressure conditions. Preferably, the extrudable composition is extruded at a temperature of from at least about 125 degrees Centigrade if the polyolefin is polyethylene or at least about 175 degrees Centigrade if the polyolefin is polypropylene, for example, from about 290 degrees Centigrade to about 345 degrees Centigrade, more specifically from about 300 degrees Centigrade to about 335 degrees Centigrade. Preferably, the extrudable composition is etruded within the above-identified temperature ranges and pressures, within the die tip, (for example, within the extrusion capillaries of a die tip having thirty (30) extrusion capillaries per lineal inch of die tip with each of the capillaries having a diameter of about 0.0145 inches and a length of 0.113 inches) of no more than about 300 pounds per square inch, gage, for example, from about 20 pounds per square inch, gage, to about 250 pounds per square inch, gage. More specifically, the extrudable composition is extruded at a pressure within the capillaries of the above-identified die tip of from about 50 pounds per square inch, gage, to about 250 pounds per square inch, gage, for example, from about 125 pounds per square inch, gage, to about 225 pounds per square inch, gage.

In the formation of elastomeric nonwoven webs, the extrudable composition is extruded, at the above-defined elevated temperature and elevated pressure conditions at a rate of from at least about 0.02 gram per capillary per minute to about 1.7 or more grams per capillary per minute, for example, from at least about 0.1 gram per capillary per minute to about 1.25 grams per capillary per minute, more specifically, from at least about 0.3 gram per capillary per minute to about 1.1 grams per capillary per minute, through a die having a plurality of small diameter extrusion capillaries, as molten threads into a gas stream which attenuates the molten threads to provide a gas-borne stream of microfibers which are then formed into the fibrous nonwoven elastomeric web upon their deposition on a collecting arrangement. The attenuating gas stream is applied to the molten threads at a temperature of from at least about 100 degrees Centigrade to about 400 degrees Centigrade, for example, from about 200 degrees Centigrade to about 350 degrees Centigrade and at a pressure of from at least about 0.5 pound per square inch, gage, to about 20 pounds per square inch, gage, for example, from at least about 1 pound per square inch, gage, to about 10 pounds per square inch, gage. The thread attenuating gas stream may be an inert, non-oxidzing, gas stream such as, for example, a stream of nitrogen gas. In some embodiments the velocity and temperature of the thread-attenuating gas stream is adjusted so that the fibers are collected as substantially continuous fibers having diameters of from about ten (10) microns to about sixty (60) microns, for example, from at least about ten (10) microns to about forty (40) microns. The fibrous nonwoven elastomeric webs so formed will include elastomeric fibers composed of from at least about 10 percent, by weight, of the block copolymer and greater than 0 percent, by weight, and up to about 90 percent, by weight, of the polyolefin. The fibers are usually composed from at least about 20 percent, by weight, to about 95 percent, by weight, of the block copolymer and from at least about 5 percent, by weight, to about 80 percent, by weight of the polyolefin. For example, the fibers may be composed from at least about 30 percent, by weight, to about 90 percent, by weight, of the block copolymer and from at least about 10 percent, by weight, to about 70 percent, by weight, of the polyolefin. Preferably, the fibers are composed from about 50 percent, by weight, to about 90 percent, by weight, of the block copolymer and from at least about 10 percent, by weight, to about 50 percent, by weight, of the polyolefin. For example, the fibers may be composed from at least about 50 percent, by weight, to about 70 percent, by weight, of the block copolymer and from at least about 30 percent, by weight, to about 50 percent, by weight, of the polyolefin.

Another such resiliently stretchable material is disclosed in U.S. patent application, Ser. No. 760,437 in the name of Jack D. Taylor and Michael J. Vander Wielen and assigned to the assignee of the present application, entitled "Composite Elastomeric Material and Process for Making the Same", the disclosure of which is incorporated herein by reference and relied upon. That application provides a method of producing a composite elastic material comprising at least one gatherable web bonded to at least one elastic web, the method comprising (a) tensioning an elastic web (which may comprise a fibrous web such as a nonwoven web of elastomeric fibers, for example, meltblown elastomeric fibers) to elongate it; (b) bonding the elongated elastic web to at least one gatherable web under conditions which soften at least portions of the elastic web to form a bonded composite web; and (c) relaxing the composite web immediately after the bonding step whereby the gatherable web is gathered to form the composite elastic material. The fibrous elastic web can also be maintained in a stretched condition during the bonding, at an elongation of at least about 25 percent, preferably about 25 percent to over 500 percent, for example, about 25 percent to 550 percent elongation during the bonding. The method also includes bonding the elongated elastic web to the gatherable web by overlaying the elastic and gatherable webs and applying heat and pressure to the overlaid webs, for example, by heating bonding sites on the elastic web to a temperature of from at least about 65 degrees Centigrade to about 120 degrees Centigrade, preferably from at least about 70 degrees Centigrade to about 90 degrees Centigrade.

That application also provides an elastic composite material comprising an elastic web bonded to at least one gatherable web which is extensible and contractible with the elastic web upon stretching and relaxing of the composite material, the elastic composite material being made by a method as described above. Also provided is an elastic web that is bonded to the gatherable web at a plurality of spaced-apart locations in a repeating pattern and the gatherable web is gathered between the bonded locations. The elastic web may comprise a nonwoven web of elastomeric fibers, preferably elastomeric microfibers, such as, for example, an elastomeric nonwoven web of meltblown elastomeric fibers or an elastomeric film.

The elastic composite material may include one or more of the following in any combination: the elastomeric fibers, preferably meltblown elastomeric fibers, may be formed from material selected from the group including (i) A-B-A' block copolymers wherein "A" and "A'" may be the same or different endblocks and each is a thermoplastic polymer endblock or segment which contains a styrenic moiety such as polystyrene or polystyrene homologs, and "B" is an elastomeric polymer midblock or segment, for example, a midblock selected from the group including poly(ethylene-butylene), polyisoprene and polybutadiene, with poly(ethylene-butylene) being preferred and (ii) blends of one or more polyolefins with the A-B-A' block copolymers of (i) where "B" is a poly(ethylene-butylene) midblock; each of the "A" and "A'" endblocks may be selected from the group consisting of polystyrene and polystyrene homologs, for example, poly(alphamethylstyrene), and where the elastomeric fibers are formed from a blend of one or more polyolefins with an A-B-A' block copolymer where "B" is a poly(ethylene-butylene) midblock, the polyolefin is selected from one or more of polyethylene, polypropylene, polybutene, ethylene copolymers, propylene copolymers and butene copolymers; the elastomeric film and the elastomeric fibers which form the elastomeric nonwoven web, for example, the meltblown microfibers, are composed of at least 10 percent, for example at least 20 percent, more specifically at least 30 percent, for example, from about 10 percent to 90 percent, by weight, of the aforesaid A-B-A' block copolymers and greater than 0 percent, by weight, for example, from about 90 percent to about 10 percent, by weight, of the polyolefin; the elastic web, for example, a fibrous elastic web, is bonded to the gatherable web at a plurality of spaced-apart locations in a repeating pattern and the gatherable web is gathered between the bonded locations; the elastic web preferably has a low basis weight of from about 5 to about 300, preferably from about 5 to about 200, grams per square meter, for example, from about 5 to about 100 grams per square meter, although its basis weight can be much higher; the gatherable web is a nonwoven, non-elastic material, preferably one composed of fibers formed from materials selected from the group including polyester fibers, for example, poly(ethylene terephthalate) fibers, polyolefin fibers, polyamide fibers, for example, nylon fibers, cellulosic fibers, for example, cotton fibers, and mixtures thereof. Alternatively, the gatherable web may be any suitable woven fabric. In a particular aspect, the composition of the A-B-A' polymer used is such that the sum of the molecular weight of "A" with the molecular weight of "A'" is from about 14 to 31 percent (from about 14 to 29 percent when "B" is poly(ethylene-butylene)) of the molecular weight of the A-B-A' block copolymer.

A further such resiliently stretchable material is disclosed in U.S. patent application, Ser. No. 760,449, in the name of Michael J. Morman, and assigned to the assignee of the present invention, entitled "Composite Nonwoven Elastic Web", the disclosure of which is incorporated herein by reference. That application is directed to a process for producing a composite nonwoven elastic web which is composed of a nonwoven elastic web that is joined to a fibrous nonwoven gathered web. In particular, the process disclosed therein produces a composite nonwoven elastic web which, in its relaxed, nonstretched state, is composed of a gathered nonwoven fibrous web that is joined to a nonwoven elastic web with the nonwoven elastic web having been relaxed from a stretched, biased length to a relaxed, unbiased, nonstretched length so as to gather the fibrous nonwoven gathered web. An important feature of the process disclosed therein is that the fibrous nonwoven gatherable web is formed directly onto a surface of the nonwoven elastic web while the nonwoven elastic web is maintained in a stretched, biased and elongated condition. The nonwoven elastic web may be formed by, for example, a meltblowing process or any other process for forming a nonwoven elastic web. For example, the nonwoven elastic web could be an apertured web of an elastic film as opposed to a meltblown fibrous nonwoven elastic web. The formed nonwoven elastic web has a normal relaxed, nonstretched, nonbiased length. Thereafter, the nonwoven elastic web is elongated by being stretched to a stretched, biased length. In a subsequent step of the process a fibrous nonwoven gatherable web may be formed, for example, by either a meltblowing or spunbonding process or any other process for forming a fibrous nonwoven gatherable web, directly upon a surface of the nonwoven elastic web while the nonwoven elastic web is maintained at its elongated, stretched and biased length. During formation of the fibrous nonwoven gatherable web the nonwoven elastic web is maintained at a stretched length which is at least about 125 percent, that is, at least about one and one quarter of the relaxed, unbiased length of the nonwoven elastic web. For example, the stretched, biased length of the nonwoven elastic web may be maintained in the range of from at least about 125 percent of the relaxed, unbiased length of the nonwoven elastic web to about 700 or more percent of the relaxed, unbiased length of the nonwoven elastic web. The fibrous nonwoven gatherable web is joined to the nonwoven elastic web while the nonwoven elastic web is maintained at its elongated stretched, biased length. This results in the formation of a composite nonwoven elastic web which includes the nonwoven elastic web which is joined to the fibrous nonwoven gatherable web. Because the fibrous nonwoven gatherable web is formed directly onto the surface of the nonwoven elastic web while the nonwoven elastic web is being maintained at its stretched, biased length, the nonwoven elastic web is, at this stage in the process, elongated, stretched and biased and the fibrous nonwoven gatherable web is in an ungathered but gatherable condition. In one aspect, the joining of the fibrous nonwoven gatherable web to the nonwoven elastic web is achieved by heat-bonding to fuse the two webs to each other. The heat-bonding may be carried out within the temperature range of from about 50 degrees centigrade below the melt temperature of at least one of the materials utilized to form at least one of the two webs to about the melt temperature of at least one of the materials utilized to form at least one of the two webs. At high through-put rates the heat-bonding can be carried out above the melt temperature of one or more of the materials utilized to form the webs. The heat-bonding may also be carried out under appropriate conventional pressurized conditions. If desired, conventional sonic bonding techniques may be substituted for the heat-bonding steps.

The application also discloses another embodiment whereby the joining of the fibrous nonwoven gatherable web to the stretched nonwoven elastic web is achieved solely by the entanglement of the individual fibers of the fibrous nonwoven gatherable web with the nonwoven elastic web during formation of the fibrous gatherable web on the surface of the elastic web. If the nonwoven elastic web is a fibrous nonwoven elastic web formed by, for example, meltblowing, entanglement of the individual fibers of the fibrous nonwoven gatherable web with the fibrous nonwoven elastic web is achieved by entanglement of the individual fibers of the fibrous gatherable web with the individual fibers of the fibrous elastic web. If the nonwoven elastic web is an apertured film, joining of the fibrous nonwoven web with the film is achieved by entanglement of the individual fibers of the fibrous gatherable web within the apertures of the film. The joining of the two webs to each other can also be achieved by forming the nonwoven elastic web out of a tacky elastic material, a process that will be discussed hereinafter. In addition, the joining of the two webs to each other may be further enhanced by applying pressure t the two webs after the gatherable web has been formed on the surface of the elastic web. Further improvement in the joining of the two webs can be obtained by applying an adhesive material to the upper surface of the nonwoven elastic web prior to formation of the fibrous nonwoven gatherable web thereon.

After joining of the two webs to each other has been achieved to form a composite elastic web, the biasing force is removed from the composite nonwoven elastic web and the composite elastic web is allowed to relax to its normal relaxed, unbiased length. Because the fibrous nonwoven gatherable web is joined to the nonwoven elastic web while the nonwoven elastic web is stretched, relaxation of the composite nonwoven elastic web results in the gatherable web being carried with the contracting nonwoven elastic web and thus being gathered. After gathering of the fibrous nonwoven gatherable web has occurred by reducing the biasing force on the composite nonwoven elastic web, the composite nonwoven elastic web may be rolled up in rolls for storage and shipment of directed to a manufacturing process for the production of products such as the disposable garments taught by the present application.

As indicated above, the process disclosed in U.S. patent application Ser. No. 760,449 can be enhanced by the utilization of a tacky fibrous nonwoven elastic web which can be formed by, for example, meltblowing microfibers of a tacky elastic material such as, for example, an A-B-A' block copolymer or blends of such A-B-A' block copolymers with poly(alpha-methylstyrene) where "A" and "A'" are each thermoplastic polystyrene or polystyrene homolog endblocks and "B" is an elastic polyisoprene midblock. In some embodiments "A" may be the same thermoplastic polystyrene or polystyrene homolog endblock as "A'". The tacky fibrous nonwoven elastic web is then elongated by being stretched to an elongated, stretched length and a fibrous nonwoven gatherable web is formed, for example, by meltblowing or spunbonding the fibrous nonwoven gatherable web, directly upon a surface of the tacky fibrous nonwoven elastic web while maintaining the fibrous nonwoven elastic web at its stretched length. As a result of the fact that the fibrous nonwoven elastic web is tacky, the fibrous nonwoven gatherable web is simultaneously formed upon and adhesively joined to the surface of the tacky fibrous nonwoven elastic web. This results in the formation of a composite nonwoven elastic web having an ungathered fibrous gatherable web adhesively joined to the tacky fibrous nonwoven elastic web with the joining of the two webs to each other being achieved by the adhesive joining which occurs during formation of the fibrous nonwoven gatherable web on the surface of the fibrous nonwoven elastic web. The adhesive joining of the two webs to each other may be increased upon application of pressure to the composite nonwoven elastic web by passing the composite nonwoven elastic web through the nip between rollers, which may be unheated, after the composite web has been formed but before the fibrous tacky nonwoven elastic web is allowed to relax. The adhesive joining may be further enhanced by application of an adhesive material to the surface of the tacky fibrous nonwoven elastic web prior to formation of the gatherable web thereon. The composite nonwoven elastic web is then allowed to relax to its normal relaxed, unbiased length. Because the fibrous nonwoven gatherable web is joined to the tacky fibrous nonwoven elastic web while the tacky fibrous nonwoven elastic web is in a stretched condition, relaxation of the composite nonwoven elastic web and thus the tacky fibrous nonwoven elastic web results in the gatherable web being carried with the contracting fibrous nonwoven elastic web and thus being gathered. After gathering of the fibrous nonwoven gatherable web has occurred the composite nonwoven elastic web may be rolled up in rolls for storage or directly applied to a manufacturing process for the production of disposable garments such as the disposable garments taught by the present application.

The U.S. patent application, Ser. No. 760,449 is also directed to a composite nonwoven elastic web composed of a nonwoven elastic web that is joined to a gatherable fibrous nonwoven web which has been gathered and with the composite web having been formed by any of the embodiments of the process disclosed above. In particular, the composite nonwoven elastic web, in its relaxed, nonstretched state, is composed of a nonwoven elastic web that is joined to a fibrous nonwoven gathered web which has been gathered as a result of the nonwoven elastic web having been relaxed from an elongated stretched, biased length to a relaxed, unbiased nonstretched length. Exemplary elastomeric materials for use in formation of the fibrous nonwoven elastic web include polyester elastomeric materials, polyurethane elastomeric materials, and polyamide elastomeric materials. Other elastomeric materials for use in formation of the fibrous nonwoven elastic web include (a) A-B-A' block copolymers, where "A" and "A'" are each a thermoplastic polymer endblock which includes a styrenic moiety and where "A" may be the same thermoplastic polymer endblock as "A'", such as a poly(vinyl arene), and where "B" is an elastomeric polymer midblock such as a conjugated diene or a lower alkene or (b) blends of one or more polyolefins or poly(alpha-methyl styrene) with A-B-A' block copolymers, where "A" and "A'" are each a thermoplastic polymer endblock which includes a styrenic moiety, where "A" may be the same thermoplastic polymer endblock as "A'", such as a poly(vinyl arene) and where "B" is an elastomeric polymer midblock such as a conjugated diene or a lower alkene. The "A" and "A'" endblocks may be selected from the group including polystyrene and polystyrene homologs and the "B" midblock may be selected from the group including polyisoprene, polybutadiene or poly(ethylene-butylene). If "A" and "A'" are selected from the group including polystyrene or polystyrene homologs and "B" is poly(ethylene-butylene), materials which may be blended with these block copolymers are polymers, including copolymers of ethylene, propylene, butene, other lower alkenes or one or more of these materials. If "A" and "A'" are selected from the group including polystyrene or polystyrene homologs and "B" is a polyisoprene midblock, a material for blending with this type of block copolymer is poly(alpha-methylstyrene).

As used in the U.S. patent application Ser. No. 760,449, and as contemplated herein, the term "nonwoven web" or "nonwoven layer" includes any web of material which has been formed without use of textile weaving processes which produce a structure of individual fibers which are interwoven in an identifiable repeating manner. Specific examples of nonwoven webs would include, without limitation, a meltblown nonwoven web, a spunbonded nonwoven web, an apertured film, a microporous web, elastomeric netting or a carded web of staple fibers.

It is to be clearly understood that the descriptions of methods for making a material suitable for outer cover 12 and the description of materials suitable for the outer cover 12 are exemplary only and not meant to be limiting. As discussed previously, the material of the laminar leg elastics 102 may also be used as the outer cover material and, conversely, the outer cover material may be used as the leg elastic material.

The bodyside liner 34 may be airlaid, a bonded carded web, a powder-bonded carded web or a pattern bonded, spunbonded web of synthetic fibers such as polypropylene, polyester and the like.

Various materials are contemplated for use as the absorbent core 38, including fibrous materials, foams, particulates, etc. In general, the most economical liquid absorbent material for use in disposable diapers has been an absorbent fiber. The absorbent fiber most commonly used is cellulosic fiber such as comminuted wood pulp, commonly known in the art as "pulp fluff," or simply "fluff."

Comminuted wood pulp (fluff) is preferred as an absorbent fiber, but other cellulose fibers such as cotton linters can be used. The preferred fluff is southern pine kraft wood pulp (i.e., made according to the sulfate process commonly known in the art) which has been bleached, such as can be purchased from International Paper Company. Other softwood fluffs may be purchased from Kimberly-Clark Corporation, such as CR-54. Various hardwood fluffs may also be blended with the softwood fluffs to form the absorbent composite. A water-swellable hydrogel material, preferably in particulate form, may be used in a number of various arrangements within the absorbent composite in order to decrease the bulkiness and enhance the capacity of the composite 38. It should be understood that additional elements could be provided in conjunction with those already set forth, without departing from the contemplated scope of the present invention and the description herein is not intended to be in any way limiting.

We claim:

1. A disposable absorbent garment comprising:
   an outer cover including a pair of leg openings, front and rear waist sections defining a waist opening, inner and outer surfaces, a central crotch portion between said leg openings and opposed front and rear panels separated by said crotch portion;
   an absorbent structure superposable on said outer cover, for absorbing and retaining bodily exudates;
   gathers at either of said leg opening and said waist opening; and
   wherein either of said leg and waist gathers are formed from a breathable elastomeric nonwoven laminar fabric comprising a liquid impervious elastomeric film carrier sheet sandwiched and bonded at spaced apart sites between two or more nonwoven facing sheets thereby forming air permeable apertures therein at said bond sites, providing a cushioned cloth-like fit of said garment about the body of a wearer.

2. A disposable absorbent garment comprising:
   an outer cover including a pair of leg openings, front and rear waist sections defining a waist opening, inner and outer surfaces, a central crotch portion between said leg openings and opposed front and rear panels separated by said crotch portion;
   an absorbent structure superposable on said outer cover, for absorbing and retaining bodily exudates;
   gathers at either of said leg openings and said waist openings; and
   wherein said outer cover is formed from a breathable elastomeric nonwoven laminar fabric comprising a liquid impervious elastomeric film carrier sheet sandwiched and bonded at spaced apart sites between two or more nonwoven facing sheets thereby forming air permeable apertures therein at said bond sites, providing a cushioned cloth-like fit of said garment about the body of a wearer.

3. The garment of claim 1 or claim 2 wherein said carrier sheet is sandwiched in an unstretched condition between creped ones of said facing sheets.

4. The garment of claim 3 wherein said carrier sheet is bonded between said facing sheets while said carrier sheet is in a substantially unstretched condition.

5. The garment of claim 3 wherein said carrier sheet is bonded between said facing sheets while said carrier sheet is in at least a partially stretched condition.

6. The garment of claim 1 or claim 2 wherein said facing sheets comprise spun-bonded, carded, spun-laced, air-laid, co-structured or meltblown webs.

7. The garment of claim 6 wherein said carrier sheet comprises an A-B-A' block copolymer.

8. The garment of claim 6 wherein said carrier sheet comprises an extrudable polyolefin.

9. The garment of claims 1 or 2, further comprising a pair of leg gathers extending along outermost portions of said leg openings and consisting essentially of said laminar fabric.

* * * * *